(12) United States Patent
Swensen

(10) Patent No.: US 11,103,278 B2
(45) Date of Patent: Aug. 31, 2021

(54) FRACTURE-DIRECTED STEERABLE NEEDLES

(71) Applicant: Washington State University, Pullman, WA (US)

(72) Inventor: John Paul Swensen, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 16/133,005

(22) Filed: Sep. 17, 2018

(65) Prior Publication Data

US 2020/0289152 A1  Sep. 17, 2020

Related U.S. Application Data

(60) Provisional application No. 62/559,346, filed on Sep. 15, 2017.

(51) Int. Cl.
| | |
|---|---|
| *A61B 17/34* | (2006.01) |
| *A61B 17/00* | (2006.01) |
| *A61B 90/11* | (2016.01) |
| *A61B 34/00* | (2016.01) |
| *A61B 34/20* | (2016.01) |
| *A61B 90/00* | (2016.01) |
| *A61M 25/01* | (2006.01) |

(52) U.S. Cl.
CPC .......... *A61B 17/3403* (2013.01); *A61B 34/20* (2016.02); *A61B 34/73* (2016.02); *A61B 90/11* (2016.02); *A61B 2017/00323* (2013.01); *A61B 2017/00867* (2013.01); *A61B 2017/3409* (2013.01); *A61B 2017/3454* (2013.01); *A61B 2090/373* (2016.02); *A61B 2090/374* (2016.02); *A61B 2090/378* (2016.02); *A61M 25/0102* (2013.01)

(58) Field of Classification Search
CPC ...... A61B 17/3203; A61B 2017/32032; A61B 17/32037; A61B 2017/320056; A61B 17/3403; A61B 2017/3409; A61B 2017/3454
See application file for complete search history.

(56) References Cited

U.S. PATENT DOCUMENTS

| | | | | |
|---|---|---|---|---|
| 2013/0109910 A1* | 5/2013 | Alexander | ............ | A61F 2/0045 600/37 |
| 2015/0112188 A1* | 4/2015 | Stigall | .............. | A61B 17/32037 600/424 |

\* cited by examiner

*Primary Examiner* — Wade Miles
(74) *Attorney, Agent, or Firm* — W&C IP

(57) ABSTRACT

The present embodiments herein relate to an improved needle design and control methodology for fractured directed guiding to a desired target. This system has the capability to control the insertion not only in 2D-plane, but also in 3D-space in a very controlled manner. A method of controlling the path of movement of a needle structure toward a target can include a stylet type of needle configuration or a water-jet needle configuration.

10 Claims, 15 Drawing Sheets

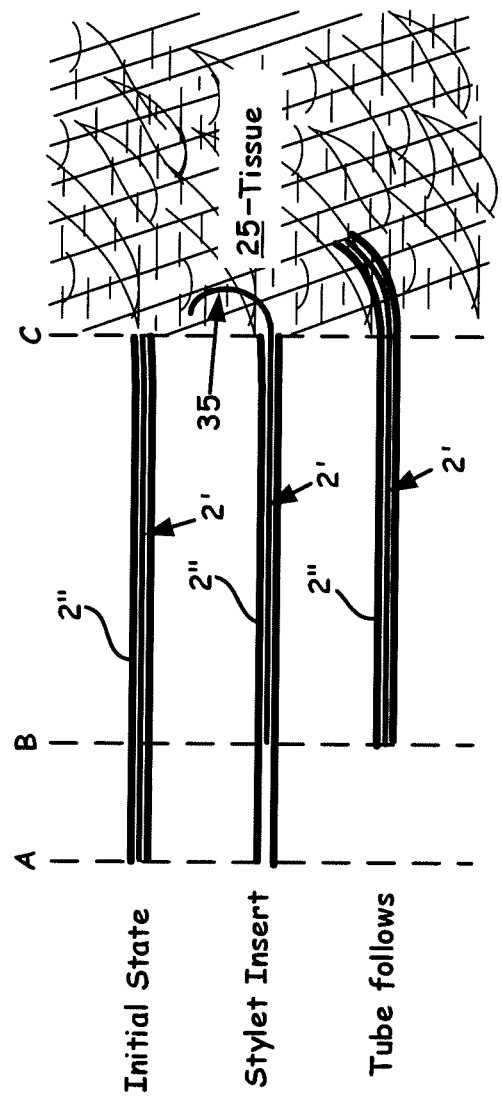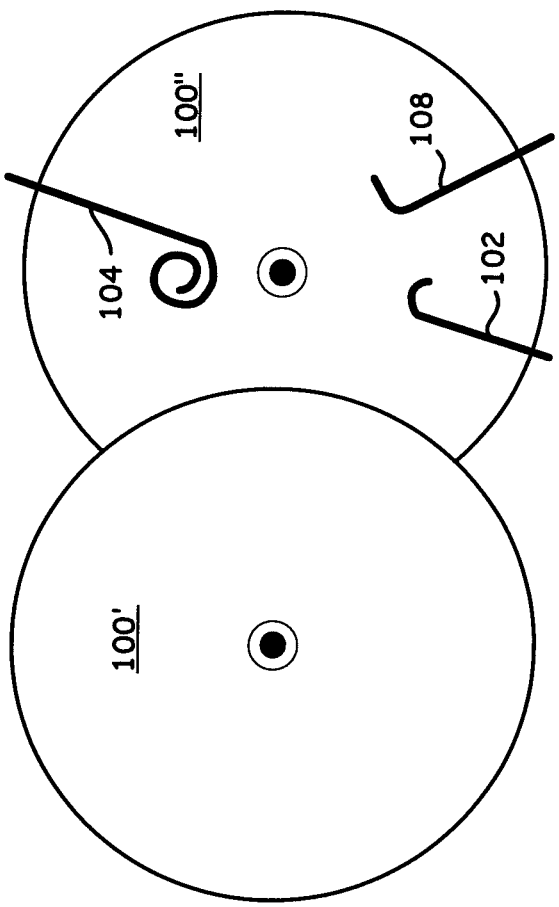

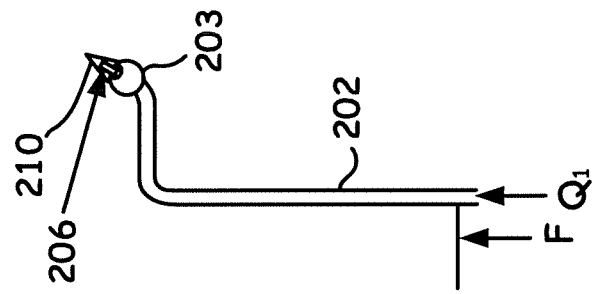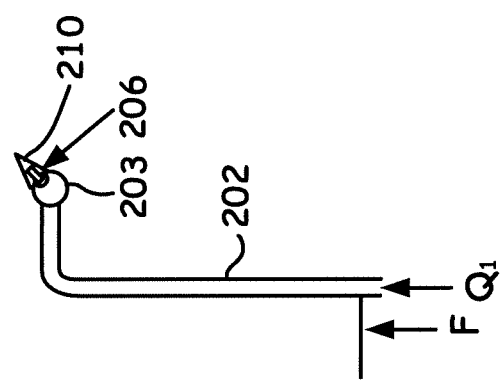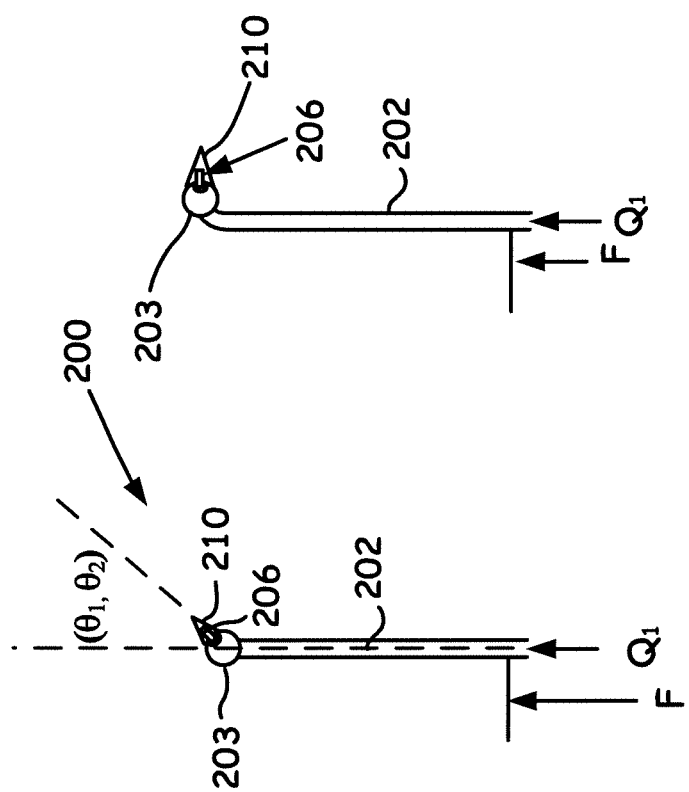
FIG. 12A  FIG. 12B  FIG. 12C  FIG. 12D

FRACTURE-DIRECTED STEERABLE NEEDLES

CROSS-REFERENCE TO RELATED APPLICATION(S)

The present application claims under 35 U.S.C. § 119, the priority benefit of U.S. Provisional Application No. 62/559,346, entitled: "FRACTURE-DIRECTED STEERABLE NEEDLES," filed Sep. 15, 2017. The disclosure of the foregoing application is incorporated herein by reference in its entirety.

BACKGROUND OF THE INVENTION

Field of the Invention

The present embodiments relates to medical devices and more particularly, to fracture-directed steerable needle devices and methods of insertion for guiding the stylet to a desired target.

Discussion of the Related Art

Cutting/fracturing occurs when energy is introduced into a material to overcome chemical bindings in the particular structure. For instance, thermal cutting methods use the energy of chemical reactions, electricity, or light to create high temperatures to melt the material at the point of cutting. Mechanical methods use the kinetic energy of the moving tool or create ductile materials by using pressure. In medical applications, needles, in particular stylet type needles, as a particular mechanical method of providing the mechanical cutting mechanism in tissues, is beneficial in that it minimizes collateral tissue damage during insertion while also reaching desired deep locations in a subject.

When a stylet type of needle is configured to mechanically cut and/or fracture tissue in a steerable arrangement, such approaches to date, can be classified into categories of bevel-tipped steering, pre-bend steering, duty-cycle steering, external lateral manipulation, active cannula (primarily for traversal of open spaces), and combinations of multiple modalities. The bevel-tipped, pre-bend, and duty-cycle classes of steerable needles are all attempting to create an asymmetric force at the tip of the needle designed to cause the tissue fracture to occur at an angle. Of these types, duty-cycle steering is an adaptation of bevel-tipped steering where the relative rate of needle rotation to the insertion distance controls the curvature as a ratio from the zero duty cycle maximum curvature to the 100% duty cycle infinite curvature.

Recent efforts have controlled the angle of a pre-bend with a fixed distal length using either tendons, with application in liver ablations, or an externally applied magnetic field, with applications in deep brain stimulation. While able to achieve the best radius of curvature to date among all methods of steerable needles, this approach still had the undesirable effect that any change in the angle at the tip of the needle, with the requisite forces to achieve tissue deformation, will necessarily cause large displacements in the tissue directly surrounding the tip. The magnitude of this deformation depends on the fulcrum length of the distal portion beyond the actuated joint and the softness of the tissue. Duty-cycle methods also must account for the inherent torsional windup associated with twisting a long, superelastic needle about the insertion axis.

Another popular technique used for both bevel-tipped steerable needles and duty-cycle steerable needles has been to find ways to selectively reduce the bending stiffness of the steerable needle in one rotational degree of freedom. One approach has been to create notched needles that effectively reduce the bending stiffness in the plane of the notched section. This is among a whole class of designs that attempt to selectively reduce the stiffness in a portion of the needle through creating thinner geometries along the length of the needle, often near the tip and sometimes with variable geometry.

Background information on an example system and method that provides for distal tip manipulation with a pre-bent stylet can be found in U.S. Pat. No. 6,592,559, entitled, "Hollow, curved, superlastic medical needle," to Pakter et al., filed Dec. 9, 1999, including the following: "[a] needle assembly 10 comprising a needle 11 that includes a needle cannula 13 made of a superelastic material such as nitinol. The needle cannula is cold-worked or heat annealed to produce a preformed bend 16 that can be straightened within passageway 21 of a coaxial outer cannula 12 for introduction into the body of a patient. Upon deployment from the outer cannula, the needle cannula substantially returns to the preformed configuration for the introduction or extraction of materials at areas lateral to the entry path of the needle assembly. The needle assembly can comprise a plurality of needle cannulae than can be variably arranged or configured for attaining a desired infusion pattern."

Background information on another example needle guidance system and method that incorporates a pre-bent stylet can be found in U.S. Pat. No. 7,662,128B2, entitled, "Steerable Needle," to Sacludean et al., filed Dec. 18, 2003, including the following: "[i]n use the cannula 100 of needle 102 of the present invention is steered by rotating the stylet to the desired orientation about the longitudinal axis 104 of the cannula 100 and advancing the stylet 101 along the longitudinal axis 104 of the cannula 100 to expose at least a part 103B of the curved portion 103 of the stylet 101 . . . . Once a fraction (extended part) 103B of the curved portion 103 of the stylet 101 is exposed, pushing the cannula 100 and stylet 101 together into the tissue while keeping the exposed part of the stylet 103B in extended position e.g. at a constant length will deflect the cannula and stylet and/or displace the deformable surrounding tissue so that the stylet tip 103A moves in the direction of the exposed or extended curved portion 103B of the stylet 101 i.e. the open end 100B of the cannula id deflected toward the tip 103A as indicated schematically by the shift in axis direction as shown at 104B in FIG. 3C. Retracting the stylet 101 into the cannula (or advancing the cannula with respect to the stylet if such action is provided for in the structure) will retract the extended portion 103B of the curved part 103 of the stylet, allowing the needle to continue being inserted in an essential straight manner but with the leading end 100B of the cannula moving in an adjusted direction determined by amount or length of the exposed or extended portion 103B."

It is also to be noted that another mechanical/medical method of cutting and/or fracturing is water-jet cutting. Such an arrangement is beneficial in that it delivers energy in the form of a high-speed liquid material applied to a work piece/subject (tissue). The water acts as a cooling agent while also providing a very high quality cut-low kerf (i.e., the width of material that is removed by the cutting process), and with low surface roughness. The use of high-pressure water in industry itself dates back over a century. In the mid-1880s, water-jet technologies were used in hydraulic mining to flush out coal from the working surface of a mine but through time have also been used for cutting plastic, high-strength alloys, metals, stone, wood, and food products.

With respect to medical applications in particular, two types of water-jets are of note, pure/plain water jet (PWJ), where cutting is done by a high velocity water (high kinetic energy of water) and abrasive water jet (AWJ), where plain water jet is generated in the orifice and flows through a mixing chamber that generates a vacuum pressure. However, while water-jet techniques have been used, for example, to dissect organs, for soft tissue resection, bone cutting, wound debridement, and surgery (renal and Glioma surgical procedures), such methodologies/systems have not to this date explored the use of water-jet cutting as a steerable-type needle device for medical applications.

Accordingly, a need exists of improving the accuracy of both therapies and biopsies via steering to a target location around obstructions, correcting for disturbances, and accounting for movement of internal organs. In addition, a need exists for providing a needle configuration and methodology that can achieve a substantially straight trajectory, even in the presence of tissue changes and membranes, but also with the capability of providing a level of steerability unobtainable with existing tip-steerable needle techniques discussed above. The embodiments herein are directed to such needs.

SUMMARY OF THE INVENTION

It is to be appreciated that the present example embodiments herein are directed to a fracture-directed steerable needle methodology and needle structure. As a first aspect, a methodology to steer a needle structure to a target includes: a) inserting a needle structure within a tissue media, wherein the needle structure further comprises: a defined spiral stylet disposed in a hollow tube, and wherein at least one of the spiral stylet and tube can be rotated about an axis; b) step and/or continuously projecting outwardly the spiral stylet from a distal end of the hollow tube into the tissue media to provide a fractured path within the tissue media while holding the hollow tube fixed, wherein the spiral stylet conforms to a spiral preformed configuration to aid steering within the media; c) holding the spiral stylet in a fixed position; d) following the fractured path provided by the path spiral stylet while the spiral stylet remains fixed so as to substantially retract the stylet within the hollow tube; and e) repeating steps b-d until the desired target is reached.

A second aspect disclosed herein is directed to fracture-directed method of steering a needle structure toward a desired target, comprising: a) inserting a needle structure within a tissue media, wherein the needle structure further comprises: a cannula fluid conduit coupled to a nozzle at a distal end, wherein the nozzle is configured to eject a desired fluid flow rate so as to provide a water jet; b) rotating the nozzle angle to control the needle structure direction; c) pulsing and/or continuously providing the desired fluid flow rate to provide a fractured a fractured path within the tissue media in the direction of the water jet; d) externally pushing the needle along the fractured path with a force; e) continually updating an angle of the nozzle of the nozzle so as to direct the needle to a determined path; and f) repeating steps b-e until the desired target is reached.

Accordingly, as briefly discussed above, the embodiments disclosed herein improves the accuracy of both therapies and biopsies via steering to a target location around obstructions, correcting for disturbances, and accounting for movement of internal organs. Such embodiments can achieve a substantially straight trajectory, even in the presence of tissue changes and membranes, but also with the capability of providing a level of steerability unobtainable with existing tip-steerable needle techniques discussed above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows a principle of the fracture-directed steering method of operation.

FIG. 2B shows some preferred examples of stylet shapes in an aluminum mold.

FIG. 12A illustrates an alternative method of operation that allows steering with a steerable needle that has a fully articulated nozzle at the tip.

FIG. 12B also illustrates an alternative method of operation that allows steering with a steerable needle that has a fully articulated nozzle at the tip.

FIG. 12C also illustrates an alternative method of operation that allows steering with a steerable needle that has a fully articulated nozzle at the tip.

FIG. 12D also illustrates an alternative method of operation that allows steering with a steerable needle that has a fully articulated nozzle at the tip.

DETAILED DESCRIPTION

Figure 1:
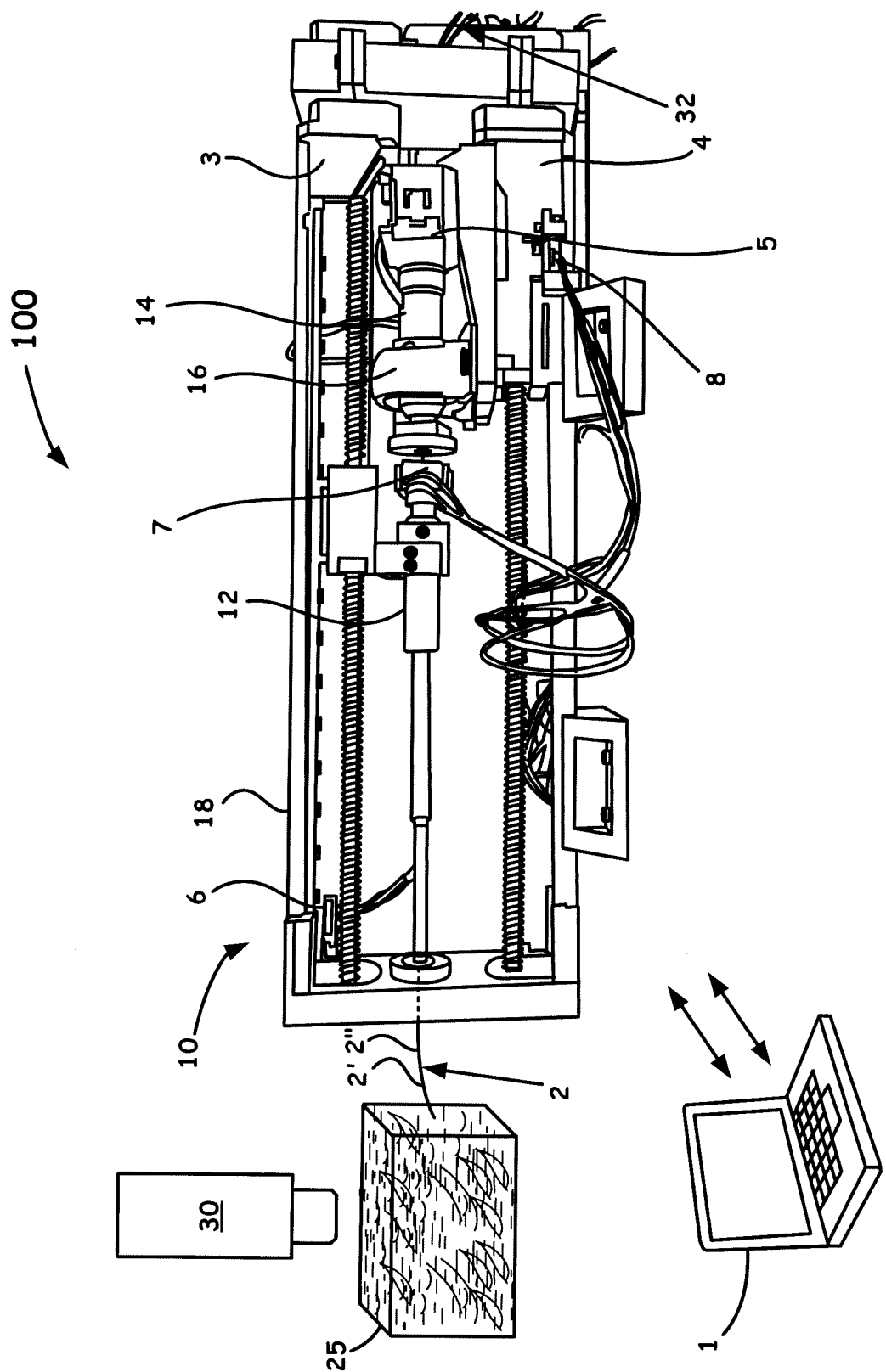
FIG. 1 shows an example embodiment of fracture-directed steering system.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. It is to be noted that as used herein, the term "adjacent" does not require immediate adjacency. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

A beneficial aspect of the embodiments herein are directed to a steerable needle insertion system/methodology wherein the embodiment first controls the direction of tissue fracture with an inner stylet and later follows with a hollow needle. Such a system/methodology is beneficial because of a provided radius of curvature down to about 3.1718 mm across a range of tissue stiffnesses and wherein the radius of curvature is controllable from a lower bound up to a near infinite radius of curvature based on a stylet/needle step size. Because of the design(s) shown herein, such a steerability aspect accounts for variability in tissues during a typical procedure and achieves radii of curvature unattainable through current bevel-tipped techniques.

In particular, the use of the stylet disposed in the hollow tube (e.g., a cannula) is configured in a manner wherein the stylet is extended from the tube while the tube is held fixed and then the tube follows while holding the stylet fixed. Such an approach enables the controlled direction of tissue fracture through the geometric design of the stylet coupled with the methodology of following the tissue fracture with the needle (tube). Such a stylet/(tube, needle, cannula) configuration, as coupled to an actuation system (often but not necessarily, a linear actuation system), provides fine control of the tissue-fracturing angle to the operator, to include human and/or computer aided guidance control means.

As another beneficial embodiment, the needle is reconfigured as a water-jet (e.g., a pure/plain water jet (PWJ)) for the insertion applications as coupled to an actuator assembly, often but not necessarily, a linear actuator assembly similar to the stylet-needle embodiment briefly discussed above and as detailed herein. Without being bound by theory in practice of the invention, when no water jet is being used, the diameter of the needle is small enough that insertion similar to a standard needle is possible. Upon reaching a point where the needle needs to "steer" or make a turn, the angle of the nozzle is set to be directed to another direction by mechanical and/or magnetic means and a high-pressure, high-velocity stream of water is pulsed to cause a fracture in the tissue. Subsequent insertion of the needle causes the needle to follow the path of tissue fracture. Such a process is repeated as the needle needs to fracture and traverse the tissue. When utilized in, for example, a medical intervention, the fracture of tissue and following the fracture is to be provided a continuous process.

It is also to be noted, as discussed briefly above, water-jet cutting is beneficial because the water acts as a coolant and correspondingly, the temperature-related damages to the surrounding tissues is virtually non-existent, as seen with thermal ablation, grinding, or sawing. Second, water-jet cutting is precise, fast, and removes minimal material, where the water washes out the debris and leaves low-roughness surfaces. Using water-jet during surgery also decreases bleeding It is additionally to be appreciated that the nozzles at the tip of the configurations to provide the water-jet action, enables sub-millimeter cutting/fracturing that is also controllable using means to achieve high dexterity needle steering. To provide such sub-millimeter cutting/fracturing, the configurations of the diameters of the needles disclosed herein are often, but not necessarily about 0.75-1 mm, while the diameter of the nozzle is 1.5-2 mm, and wherein the outlet of the nozzle is about 120 microns up to about 200 microns in diameter. It is also to be understood without being bound be theory that while PWJ is often the desired mechanism/design, other water jet cutting mechanism/designs, such as, abrasive-water jet (AWJ) nozzles and coupled systems, can also be utilized without departing from the scope and spirit of the invention. In operation, the water-jet first controls the direction of tissue fracture and the needle then follows.

Specific Description

Turning now to the figures, FIG. 1 illustrates an example fracture-directed system, generally referenced by the numeral 100. Such a system 100 which can be utilized with a stylet (e.g., a flexible resilient often cylindrical material) and a tube (cannula, needle) form aspect of the fracture-directed steerable needles, can also be reconfigured to be utilized with the water-jet configurations, as disclosed herein. Moreover, while the system 100 as shown in FIG. 1 is beneficial for illustrative purposes of a fracture-directed system 100 for any of the disclosed needle designs, it is also to be noted that other alternative configurations (geometries)/components to provide alternative arrangements/methodologies can also be utilized if capable of meeting the particular requirements of the embodiments disclosed herein without departing from the spirit and scope of the present invention.

To illustrate to the reader an example embodiment, the system 100, as shown in FIG. 1, includes a needle 2, generally shown as a coupled inner elastic wire stylet 2' (configured with a beveled end) and an often substantially but not necessarily straight outer elastic tube 2" (generally denoted) arranged as part of an insertion apparatus 10. Other distal end designs for the stylet 2' can include a trocar or a lancet configuration. It is also to be understood that the tube can also have beveled or sharpened distal end. With respect to the design of the needle 2, the stylet 2' has a beneficial radii of curvature, as generally shown in FIG. 1 but as shown with more detail in accompanying figures (e.g., see FIG. 2A), wherein a beneficial minimum radius of an example 0.47 mm diameter stylet that was without plastic deformation is at least 3.1718 mm.

The main part of the fracture-directed system 100 embodiments disclosed herein also includes a controller and data system 1 (e.g., an attached embedded microcontroller, receiving high-level commands from a computer), a pair of linear slides (i.e., an upper linear slide 3 and a lower linear slide 4) and one servo motor 5. Other components to generally illustrate the system 100 include limit switches (an advance limit switch 6, a middle limit switch 7, and a retreat limit switch 8), collets (a tube collet 12 and a wire (stylet 2') collet 14) and bearings 16 connected to a frame 18 configured from, for example, 3D printed parts and/or machined or molded components coupled together with fasteners known in the art (e.g., threaded fasteners).

To achieve high steerability inside tissues 25, there are three separate motions needed. First, the stylet 2' with a predefined geometry, such as a beneficial (spirilet) geometry, and the tube 2" that encases the stylet 2' must be able to be moved relative to each other. Second, the stylet 2' and tube 2" need to be rotated simultaneously. Through these two motions, steerability in 6 degrees of freedom can be achieved. To enable this, the linear slides 3, 4 and the servo motor 5 are often controlled by microstep drivers (not shown) to achieve accurate linear motion and rotation. Automatic motor control is often accomplished through communication means (wireless and/or hardwire means (e.g., 32)), to include RS-232 and USB, as directed by a user of the system 100 often via the controller and data system 1. In a working example embodiment of the fracture-directed system 100 of FIG. 1, the control of system 100 was accomplished through firmware running on a chipKit uC32 microcontroller (Digilent Inc., Pullman, Wash., USA), which accepts simple linear and rotational velocity commands from a PC running control scripts in the Python environment. The microcontroller (e.g., a controller and data system 1) is noted to be continually monitoring the status of the limit switches 6, 7, 8 to ensure no portion of the system 100 is driven past its physical limits.

It to be noted that while FIG. 1 shows the controller and data system 1 generally depicted as a laptop computer (also denoted with bi-directional arrows to depict communication with rest of system 100), it is to be emphasized that the operation of components within system 100 or any other embodiment disclosed herein can equally be enabled by a controller and data system of various circuitry of a known type. Such a control and data system 1 (computing devices) can thus be in the form of a desktop computer or a laptop computer as shown in FIG. 1, or can be implemented by any one of or a combination of general or special-purpose processors (digital signal processor (DSP)), firmware, software, graphical user interfaces (e.g., LabVIEW), and/or hardware circuitry to provide instrument control (e.g., AC and DC power), data analysis, etc., for the example configurations disclosed herein. It is also understood that the system 100 of FIG. 1 can be controlled remotely (e.g., from another room) and/or the information (e.g. data analysis) can be wirelessly communicated to remote servers to include the cloud via IEEE, Bluetooth, Ultra-wideband, etc., when desired for convenience of information gathering or external analysis.

It is also to be noted that in using such example computing devices, it is to also to be appreciated that as disclosed herein, the incorporated individual software modules, components, and routines may be a computer program, procedure, or process written as source code in C, C #, C++, Java, Python, and/or other suitable programming languages. The computer programs, procedures, or processes may be compiled into intermediate, object or machine code and presented for execution by any of the example suitable computing devices discussed above. Various implementations of the source, intermediate, and/or object code and associated data may be stored in one or more computer readable storage media that include read-only memory, random-access memory, magnetic disk storage media, optical storage media, flash memory devices, and/or other suitable media. A computer-readable medium, in accordance with aspects of the present invention, refers to media known and understood by those of ordinary skill in the art, which have encoded information provided in a form that can be read (i.e., scanned/sensed) by a machine/computer/processor and interpreted by the machine's/computer's/processor's hardware and/or software. It is also to be appreciated that as used herein, the term "computer readable storage medium" excludes propagated signals, per se.

Such a fracture-directed system 100 also often includes a visualization/navigation system 30 to monitor needle insertion 2 into a subject 25 (generally shown as a block of tissue mimicking phantom). As a non-limiting arrangement, the visualization/navigation system 30 can employ imaging hardware and associated software coupled to the controller and data system 1 so as to utilize at least one imaging technique to include: ultrasound, fluorescence (via injecting a dye (e.g., a water dye) into the tissue media being interrogated, tomography, and/or magnetic resonance for guidance of the needle 2 during operation of the system 100. Moreover, without being bound by theory but as an additional embodiment, a skilled user can place one or more intra-operative sensing devices (e.g., an x-ray imaging sensor) in an optimized manner (e.g., computed paths for sensor placements) for real-time feedback so as to additionally minimize intersecting obstacles (bones, organs) in order to account for needle 2 motion/direction uncertainty.

It is also to be appreciated that the system 100 disclosed herein is configured to operate as a continuum robot wherein the elastic tube 2" and stylet 2' can change its own direction and curvature while inserting. Directions are thus often controlled (via a user) by rotation of the needle 2 (i.e. simultaneous rotation of the stylet 2' and tube 2' and curvatures are controlled by step length of insertion. By using different pre-curved shapes of the stylet tip, various maximum curvatures are available.

The embodiments herein, in addition to insertion and rotation speed path needle 2 control, also enable needle 2 path control through duty-cycled rotating of the needle 2 during insertion. As utilized herein for all disclosed embodiments to include water jet embodiments, duty cycling is an amount of time that the needle 2 (e.g., the stylet 2') rotates as a percentage of total needle 2 advancement time (e.g., from 0% up to 100% duty cycling). To illustrate, if the needle 2 (e.g., the stylet 2') as disclosed herein, is advanced with a 10% duty cycle, the stylet 2' is advanced under rotation 10% of the time and without rotation 90% of the time. Duty cycling the needle can also thus be periodic in that the total advancement time can be broken down in to periods, e.g., seconds or fractions of seconds and the duty cycling can occur within those periods.

Accordingly, the use of duty cycling by any of the steerable needle embodiments disclosed herein also adjusts the curved trajectory of the advancing needle 2 by alternating between periods of insertion without rotation and periods of insertion with rotation. When the needle (e.g., a bevel tip stylet 2 or a waterjet tip structure to be detailed herein) is inserted without rotation, the needle follows a trajectory with some natural curvature that is dependent on needle characteristics (e.g., stiffness and bevel angle) and tissue characteristics (e.g., density, consistency, homogeneity). When the needle is advanced with a sufficient rotational velocity, straight trajectories can be achieved.

As alternatives to using a bevel-tipped steerable needles and duty-cycling, the embodiments herein also can be configured as needles with a bending stiffness in one rotational degree of freedom. Accordingly, a resultant notched design effectively reduces the bending stiffness in the plane of the notched section by creating thinner geometries along the length of the needle, often near the tip and sometimes with variable geometry.

Turning back to FIG. 1 with respect to an illustrative method of operation as to basic workings of system 100, it is to be noted that often the tube 2" is stiffer than the stylet 2'. Accordingly, when the stylet 2' is retracted within the hollow tube 2" structure, the curved structure of the stylet 2' is constrained by the tube 2". When the stylet 2' is projected outwardly from the end of the tube 2", the outwardly projected portion of the stylet 2' conforms to its pre-designed curved nature, as detailed herein. As part of the process, the user of system 100 determines the amount of the length of the exposed part of stylet 2' of which can be at least centimeters (e.g., 0.4 cm) in length when configured to provide such lengths. To enable such projections and retractions of the overall needle design 2, the process often is as follows: A) the wire platform as generally shown in FIG. 1, moves in a backward direction until a retreat limit switch 8 is activated, then the tube collet 12 follows the needle 2 platform to move back until an inter-stage limit switch (e.g., middle limit switch 7) is activated, then B) a preliminary step length of the stylet 2' is set for insertion as to be discussed herein with respect to accompanying figures, after which the tube 2" follows, thereafter C) a rotation angle is, if necessary, is sent by the a controller and data system 1 to the servo motor 5 to rotate the tube and wire and thus the stylet 2', thereafter steps B and C are often but not necessarily repeated until the tip of the stylet 2' reaches the desired position. To modify the plane of curvature within the tissue, the stylet 2' and tube 2" are often but not necessarily rotated simultaneous to affect the plane in which the fracture will occur during the next insertion of the stylet. This stepped process of stylet 2' and tube 2" motion, in conjunction with re-orientation of the fracture plane, achieves full control over needle 2 motion.

FIG. 2A thus is illustrative of the fracture-directed steering principle of operation. At the indicated initial state, the stylet 2' and tube 2" encasing the stylet 2' are both positioned to come into contact with tissue 25 (denoted as a dashed line at plane C). First, during the stylet Insert step (as indicated in FIG. 2A), the inner stylet 2' is advanced to fracture the tissue 25 but the tube 2" remains, as generally shown by moving the stylet 2' from the position indicated at A to the position indicated at B. Note that because of this advancing of stylet 2', as was discussed above, as the stylet 2' is projected outwardly from the end of the tube 2", the outwardly projected portion 35 of the stylet 2' conforms to its pre-designed curved nature to provide part of the steering functionality. Thereafter, as also shown in FIG. 2A, the tube thereafter follows wherein the stylet 2' can be retracted (substantially) within the hollow tube 2" As part of the process, the user of system 100 determines the amount of the length of the exposed part 35 of stylet 2' of which can be centimeters (e.g., 0.4 cm) in length down to microns when configured to provide such projections followed by the outer tube 2" to the position indicated at B.

Accordingly, it is to be noted that the premise of the operational methodology herein is that the inner stylet 2' is advanced, followed by the outer tube 2″. Because of this operation, the shape of the tissue 25 fracture closely matches the geometry of the inner stylet. After the outer tube 2″ follows the inner stylet 2′, the resulting tip position depends on the static equilibrium of the wire, tube, and tissue.

The disclosed beneficial radii of curvatures (e.g., at least 3.1718 mm) may still have an undesirable effect that any change in the angle at the tip of the needle with the requisite forces to achieve tissue formation, will necessarily cause large displacements in the tissue directly surrounding the tip. Accordingly, it is to be understood that the magnitude of such a deformation can depend on the fulcrum length of the distal portion beyond the actuated joint and the softness of the tissue. To aid the reader in understanding the possible various embodiments of the present invention, the following provides reference when considering designing the apparatus/system for the fracture-directed hardware and methodologies herein, which is intended to be illustrative only, but not limiting thereof.

Recoverable Strain and Stylet Heat

Recoverable strain in the stylet is a necessary consideration when determining the minimum radius of the stylet curvature. To ensure the stylet can be fully straightened without any plastic deformation, a non-limiting but conservative superelastic strain limit of an ε of about 8% for a beneficial Nitinol material was utilized to illustrate a working embodiment, as disclosed herein. However, while the bio-compatible, superelastic alloy of Nickel and Titanium (Nitinol) is a beneficial for both the stylet 2′ and the tube 2″ for purposes of the discussion herein, such components of the needle assembly can additionally be fabricated out of any bio-compatible material, having a desired superelastic strain limit, such as, but not limited to, polymers and the like that meets the bending requirements (e.g., stiffness) for a target tissue 25. The relationship between recoverable strain limit and needle tip pre-curvature is shown by equation (1) as follows:

$$K = \frac{2\varepsilon}{D(1+\varepsilon)} \quad (1)$$

Then the calculated minimum radius of needle curve, r, is derived from equation (2) as follows:

$$K = \frac{1}{r} \quad (2)$$

Accordingly, example tube 2″ and needles (stylets 2′) used in establishing working embodiments are described in Table 1 below, wherein it is to be noted and as discussed above, a minimum radius of a 0.47 mm diameter stylet without plastic deformation is at least 3.1718 mm.

TABLE 1

Parameters of Tube and Needle

| Parameters | Tube | Needle |
|---|---|---|
| Outer Diameter (mm) | 0.8 | 0.47 |
| Inner Diameter (mm) | 0.6 | N/A |
| Length (mm) | 350 | 400 |

Molds and Heat Treatment

To establish optimal shape to a nitinol stylet 2′ tip, all pre-curved nitinol stylet 2′ are put in an aluminum mold and then get heat-treated, such as, for example, at 500 C for 240 seconds then quenching. FIG. 2B shows the aluminum mold portion (100′ and 100″) for compression while being heat treated with three stylet geometries, an arc-stylet 102, a spirilet stylet 104, and a right angle stylet 108 indicated for forming into desired stylet shapes.

Tissue Phantoms

There were four different types of semi-transparent tissues 25 involved in establishing the working principles of operation: Shore 10 Fast, Shore 10 Medium, Shore 20 Medium and Shore 00-50. They are platinum cure liquid silicone compounds. Shore 20 Medium has the highest Shore A Hardness, 20A. Shore 10F and Shore 10M has same Shore A Hardness 10A. Shore 00-50 has the lowest hardness, 00-50. Both of 10F and 20M are mixed with 20% mineral oil by weight to reduce their hardness. 10M and 00-50 are mixed with 10% mineral oil by weight. The Tensile Strength of them is between 315 psi to 550 psi, shrinkage less than 0.001 inches/inch.

Experimental Results

Insertion Direction

Figure 3B:
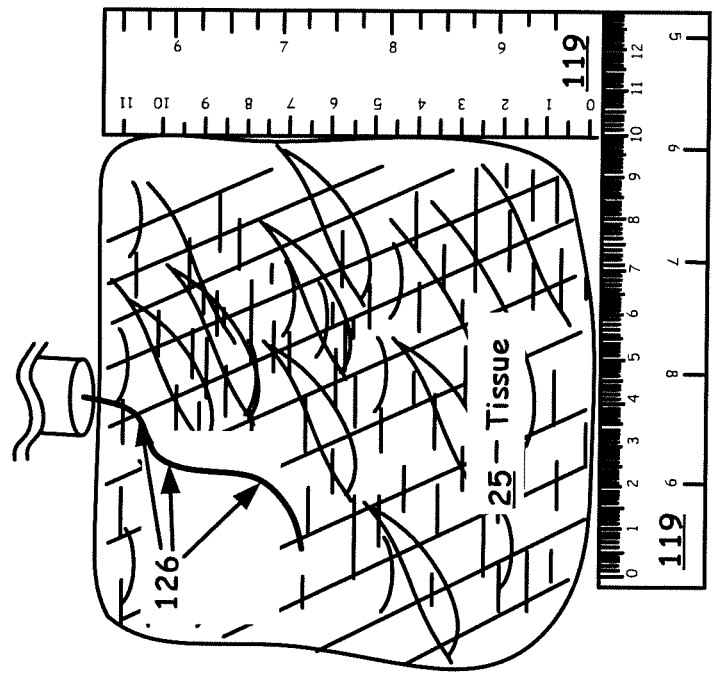
FIG. 3B illustrates triple bends into the tissue after re-orientation of the stylet.
Figure 3A:
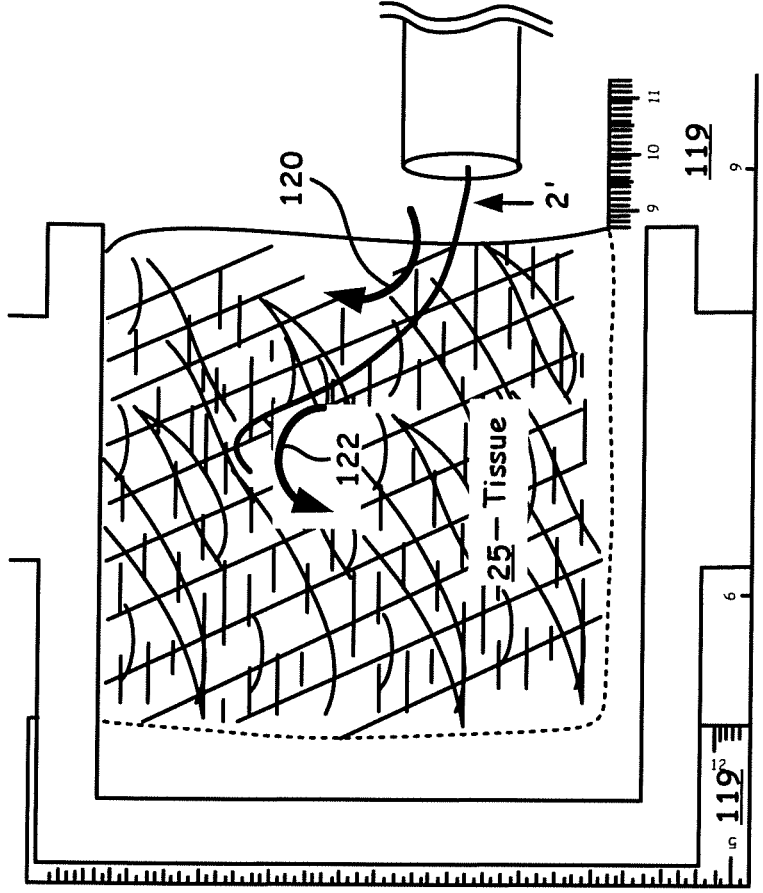
FIG. 3A illustrates that rotation of a stylet and tube can be used to change direction of subsequent stylet 2' insertions.

FIG. 3A depicts a tissue 25 phantom with ruled gratings for scaling being configured to test the parameters of the embodiments herein, wherein FIG. 3A, of which is a schematic recreation of the actual experiment, illustrates that rotation of the stylet 2′ and/or tube 2″ (not detailed) can be used to change direction of subsequent stylet 2′ insertions. The first advancement of the inner stylet 2′ in the opposite direction from the initial curvature. As shown, both stylet 2′ and tube 2″ to follow originally exhibit a clockwise curvature (as denoted by a clockwise rotating arrow 120). However, after the stylet 2′ and tube 2″ were rotated 180 degrees, the stylet's 2′ curvature is thereafter directed in the counterclockwise direction (now denoted by a counter-clockwise rotating arrow 122). FIG. 3B illustrates triple bends 126 into the tissue 25 after re-orientation of the stylet and subsequent steps. In particular, FIG. 3B shows a continued, stepped curvature with the tube 2″ (not detailed) following the stylet 2′ each step after the reorientation.

Insertion Curvature

Figure 4:
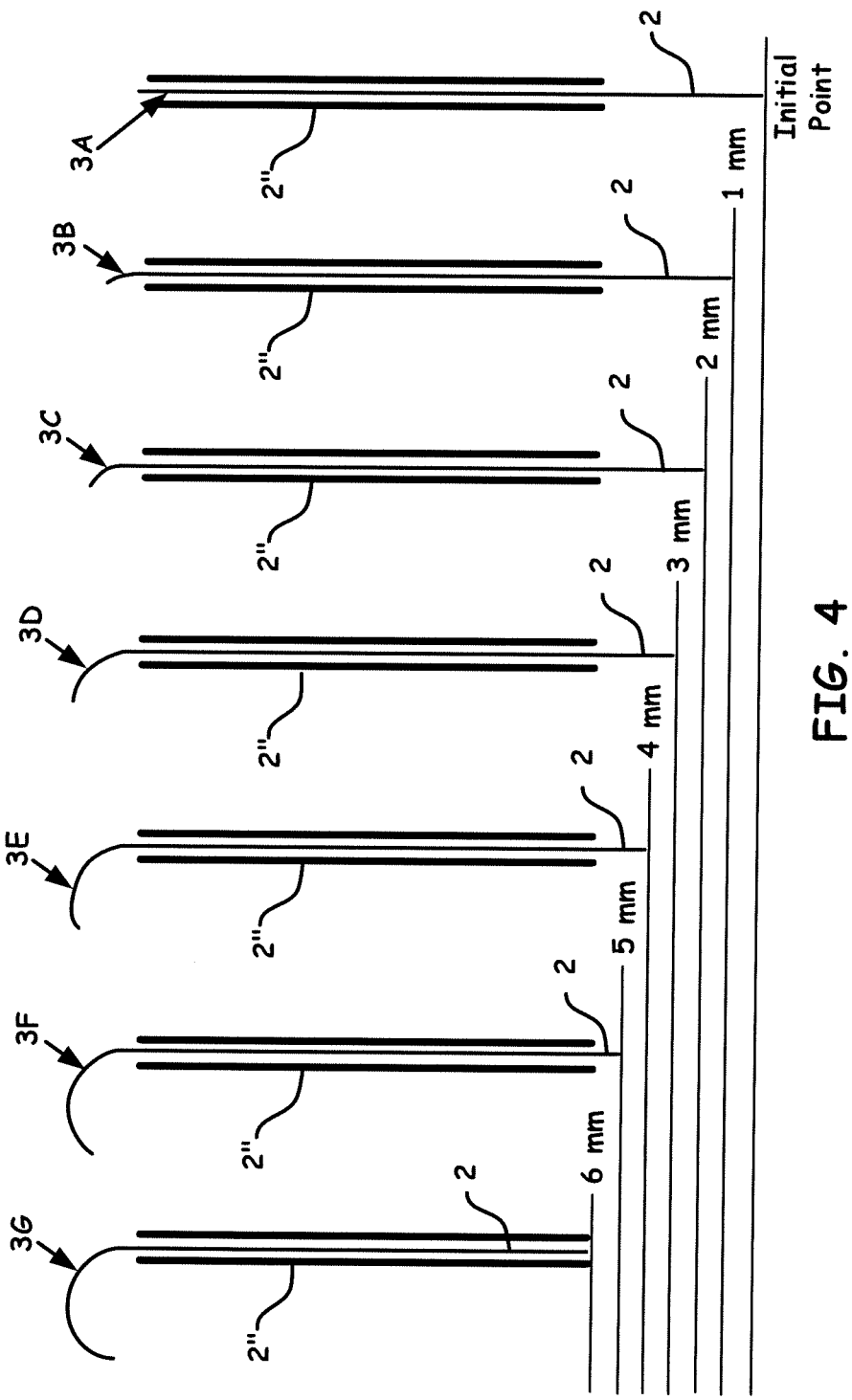
FIG. 4 shows a graphical representation of needle insertion at different step lengths.
Figure 5A:
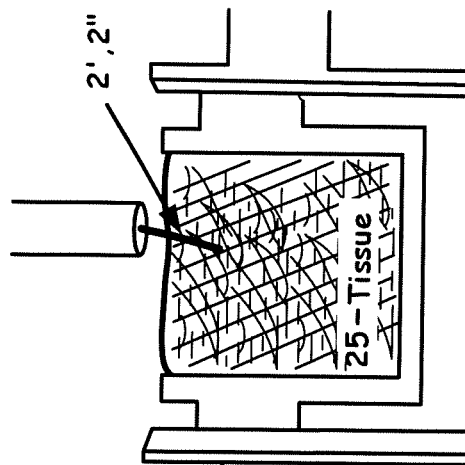
FIG. 5A shows an insertion curvature at an initial step length inside a tissue phantom, wherein changing the step length changes the curvature, as disclosed herein.
Figure 5B:
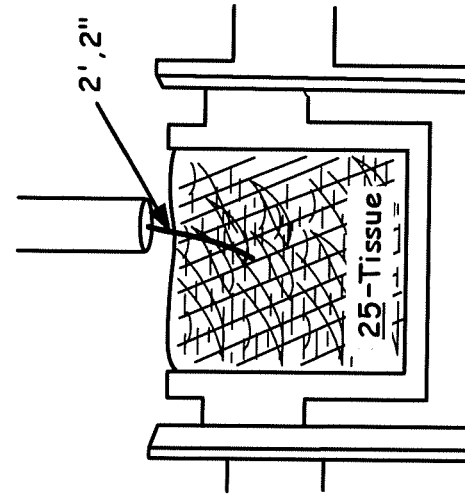
FIG. 5B shows an insertion curvature at a step length increase from that shown in FIG. 5A inside a tissue phantom, wherein changing the step length changes the curvature, as disclosed herein.
Figure 5C:
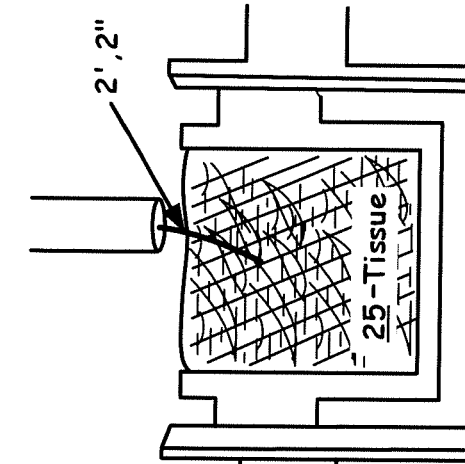
FIG. 5C shows an insertion curvature at a step length increase from that shown in FIG. 5B inside a tissue phantom, wherein changing the step length changes the curvature, as disclosed herein.
Figure 5D:
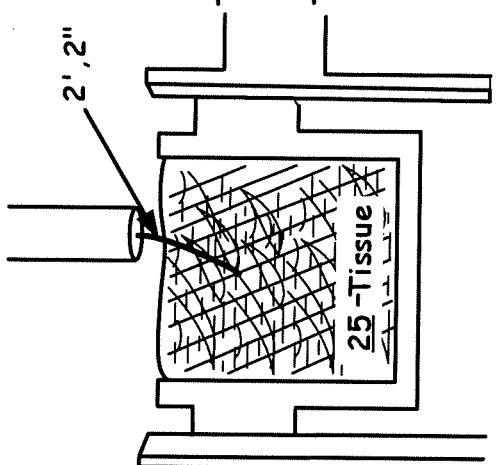
FIG. 5D shows an insertion curvature at a step length increase from that shown in FIG. 5C inside a tissue phantom, wherein changing the step length changes the curvature, as disclosed herein.
Figure 5E:
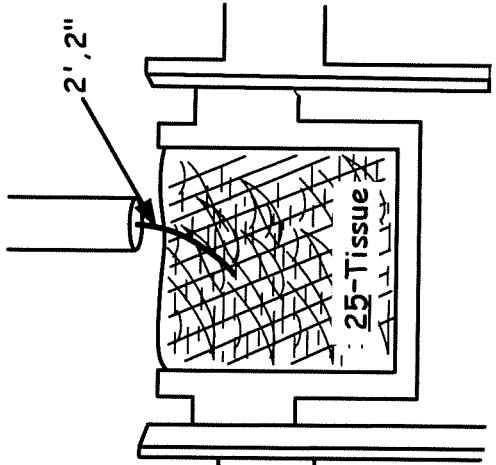
FIG. 5E shows an insertion curvature at a step length increase from that shown in FIG. 5D inside a tissue phantom, wherein changing the step length changes the curvature, as disclosed herein.
Figure 5F:
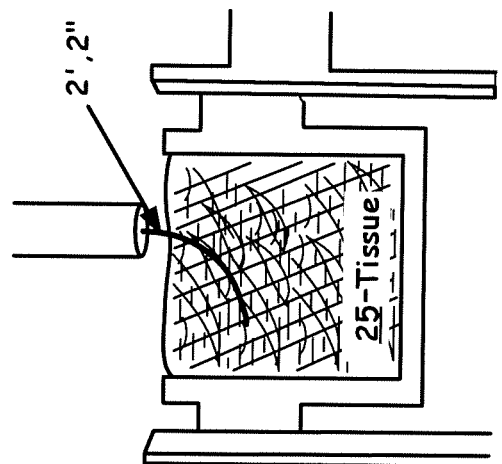
FIG. 5F shows an insertion curvature at a step length increase from that shown in FIG. 5E inside a tissue phantom, wherein changing the step length changes the curvature, as disclosed herein.

FIG. 4 illustrates how a stylet 2′ (e.g., an arc-stylet) step length within the tube 2″ will cause a longer channel to be cut in a given tissue 25, as shown in FIG. 1. In particular, as the step length increases in going from left to right (from 1 mm up to 6 mm in this example), as shown in FIG. 4, a more curved stylet 2′ comes out of tube (as shown by the denoted curved portions 3A, 3B, 3C, 3D, 3E, 3F and 3G) a corresponding further distance per step, which causes the needle curvature to rise. It is to be reiterated, as similarly briefly discussed above for FIG. 2A, that in a single insertion, there are three different states of curvature. (1) Initial state: before the insertion, the relatively low tube stiffness is not enough to straighten a pre-curved stylet 2′ completely. Some amount of curvature is evident when the tube 2″ and the stylet 2′ are fully overlapped. (2) Stylet 2′ insertion: the stylet 2′ goes into tissue, cutting a channel based on its preset curvature, and (3) Tube 2″ follows stylet 2′: the stiffness of tissue 25 is insufficient to make the tube 2″ follow the exact path of the stylet, 2′ so the resultant shape is based on the stored elastic energy of the stylet 2′, tube 2″, and tissue 25. It is thus noted that where the tube 2″ stiffness is of the same order of magnitude as the tissue 25, the actual insertion curvature is less than stylet 2′ curvature.

Figure 6:
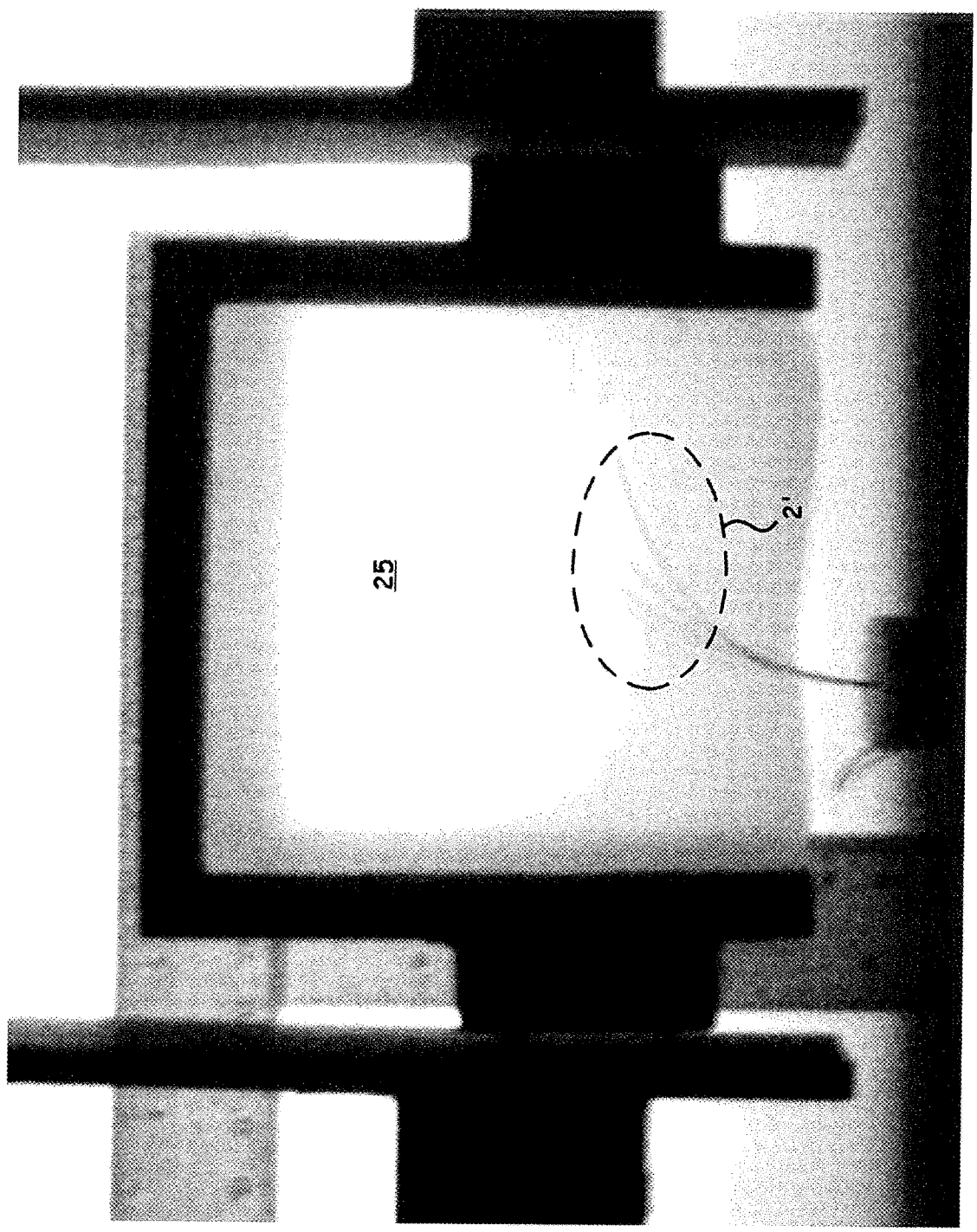
FIG. 6 shows an overlay of images to give a comparison of curvature changes with step lengths.

FIG. 5A, FIG. 5B, FIG. 5C, FIG. 5D, FIG. 5E, FIG. 5F demonstrates graphically albeit from actual experimentation, the insertion curvatures of different inner stylet 2' (e.g., an Arc-stylet) and tube 2" step lengths inside the tissue 25 phantom. Accordingly, so as to show the workings of FIG. 4 on actual tissue structures, changing the step length (e.g., centimeters down to microns) starting with a reduced step length in FIG. 5A in the same tissue 25 sample changes the curvature, as culminating in the curved structure 35 in FIG. 5F. FIG. 6 is an actual photograph of a tissue phantom 25 having an overlay of multiple trials (shown enclosed in a dashed ellipse for highlighting purposes) with differing step lengths of the stylet 2' (tube 2" not denoted) to demonstrate collectively that shown for FIG. 5A through FIG. 5F, verifying the curvature increase as the step length increases.

Curvature as a Function of Step Length

Figure 7A:
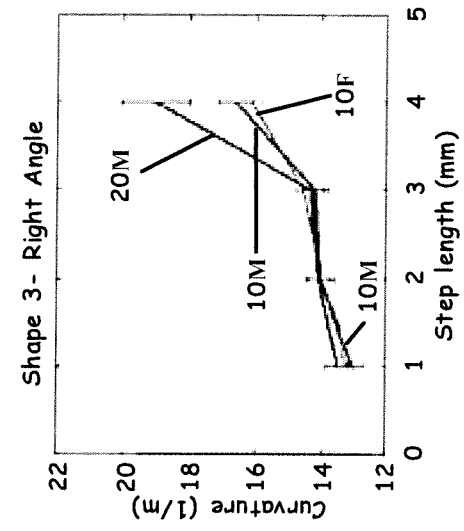
FIG. 7A shows a plot of the relatively linear relationship between curvature and radius with step length for an Arc stylet.
Figure 7B:
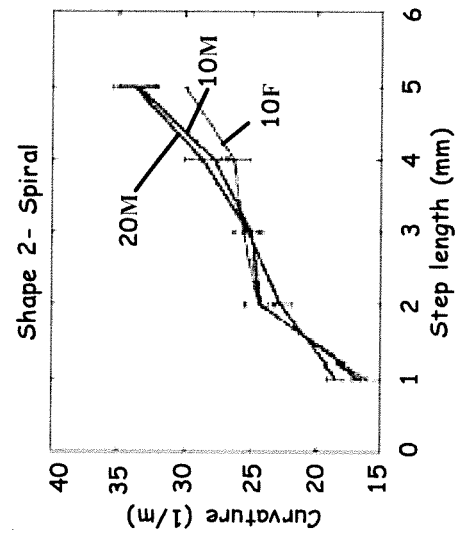
FIG. 7B also shows a plot of the relatively linear relationship between curvature and radius with step length for an Arc stylet.
Figure 7C:
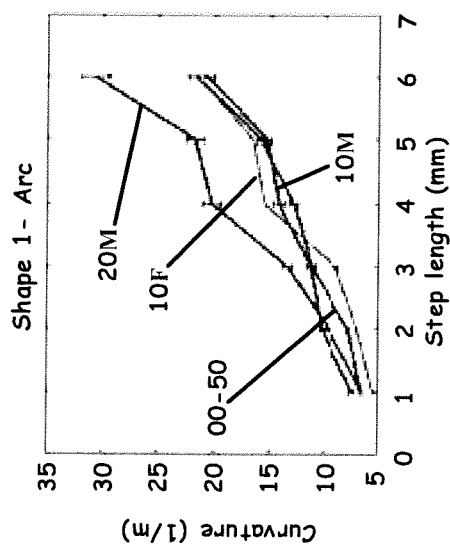
FIG. 7C shows a plot of the relationship between curvature and radius with step length for a spiral stylet.
Figure 7D:
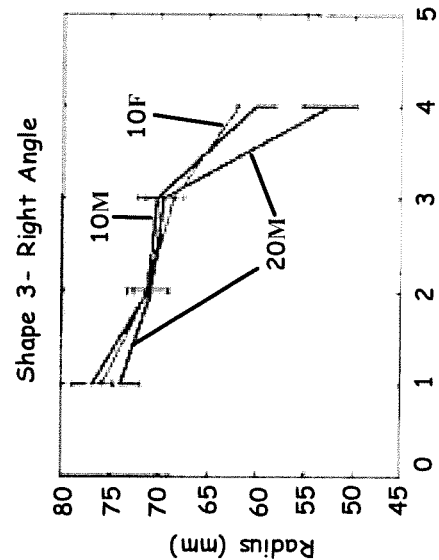
FIG. 7D also shows a plot of the relationship between curvature and radius with step length for a spiral stylet.
Figure 7E:
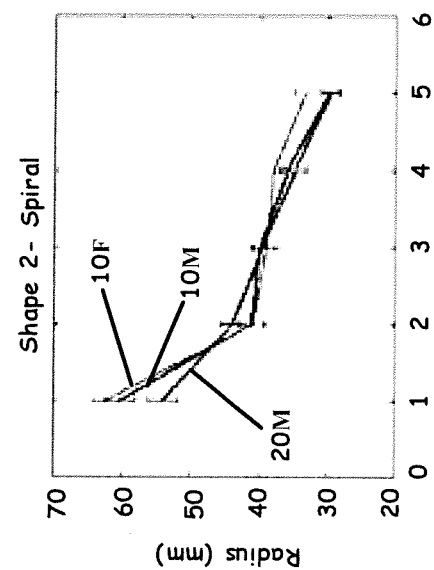
FIG. 7E shows a plot of the relationship between curvature and radius with step length for a Right Angle stylet.
Figure 7F:
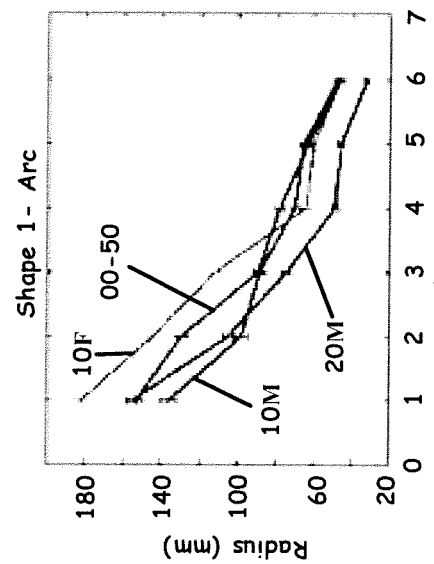
FIG. 7F also shows a plot of the relationship between curvature and radius with step length for a Right Angle stylet.

FIG. 7A, FIG. 7B, FIG. 7C, FIG. 7D, FIG. 7E, FIG. 7F demonstrates the relationship between the achievable curvature and radius with step length. FIG. 7A and FIG. 7B depict the relatively linear relationship between the curvature and radius with step lengths for four different tissue 25 phantoms for an example stylet, respectively. As evident, for different tissue phantoms, the slope of the insertion curvature as a function of step length is approximately constant, which means that the Young's modulus of the tissues has only little impact on insertion curvature for a given step length. FIG. 7C, FIG. 7D, FIG. 7E, FIG. 7F interprets the similar results as shown in FIG. 7A and FIG. 7B for a spiral stylet 2' and right-angle stylet 2', respectively. From the plots, the spiral (i.e., a spirilet) stylet 2' is the optimal geometry, both in terms of linearity and little change across tissue stiffnesses.

Figure 8B:
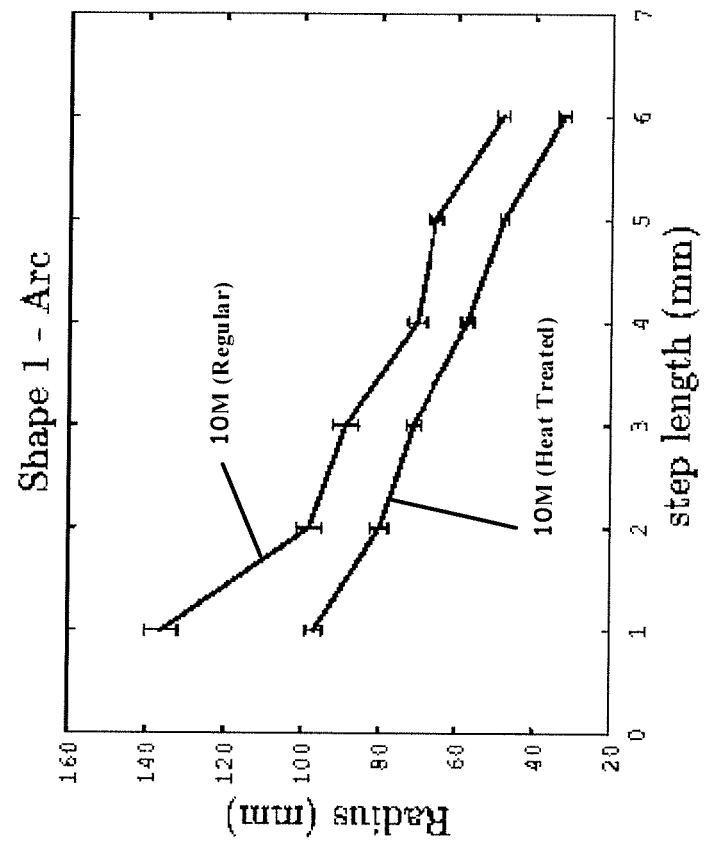
FIG. 8B shows a plot of the difference of radius between a heat-treated arc stylet and a regular arc stylet in 10M tissue phantom.
Figure 8A:
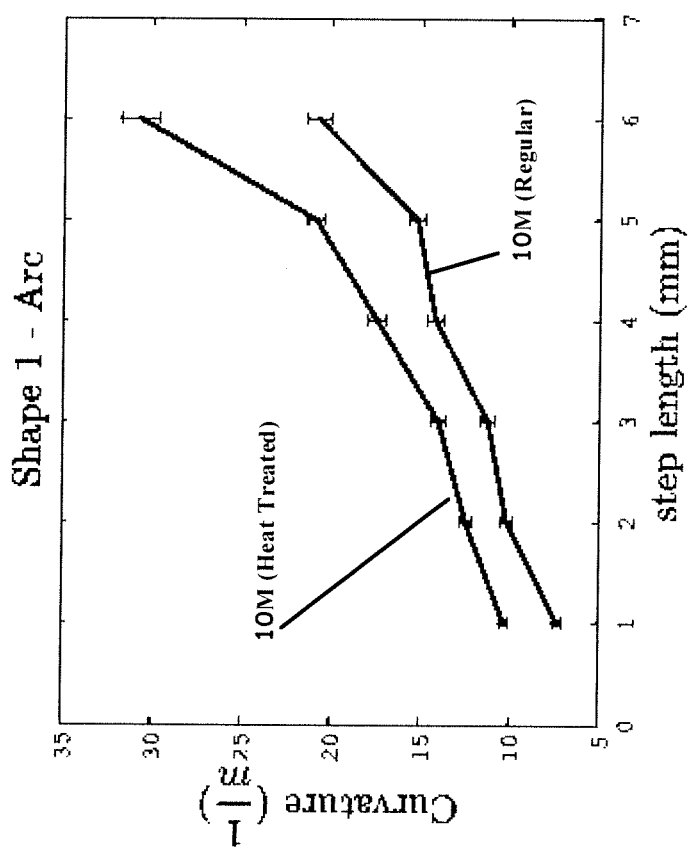
FIG. 8A shows a plot of the difference of curvatures between a heat-treated arc stylet and a regular arc stylet in 10M tissue phantom.

FIG. 8A shows a plot of the difference of curvatures between a heat treated arc stylet and a regular arc stylet in 10M tissue phantom, while FIG. 8B shows a plot of the difference of radius between a heat treated arc stylet and a regular arc stylet in 10M tissue phantom. Accordingly, FIG. 8A and FIG. 8B indicate that with a lower stiffness stylet 2', we will be able to get a better curvature in the same tissue phantom. As it is shown in Table 2, Young's Modulus of all tissues are between 0.134 Mpa to 0.97 Mpa, while Young's Modulus of a nitinol stylet 2' is about 40 Gpa.

TABLE 2

| Tissue | Approximate Young's modulus (MPa) | Shore Hardness |
|---|---|---|
| 00-50 | 0.134 | 00-50 |
| 10 Fast | 0.687 | 10A |
| 10 Medium | 0.687 | 10A |
| 20 Medium | 0.970 | 20A |

Further investigations into heat treatment to reduce the Young's Modulus of nitinol needles to a larger degree will not only get better curvatures but also control the insertion with higher accuracy. The heat treatment approach utilized herein maintains temperature at 525° C. for two hours and subsequent slow cooling to room temperature while in the stove.

Modeling of pre-curved needle System

Figure 9:
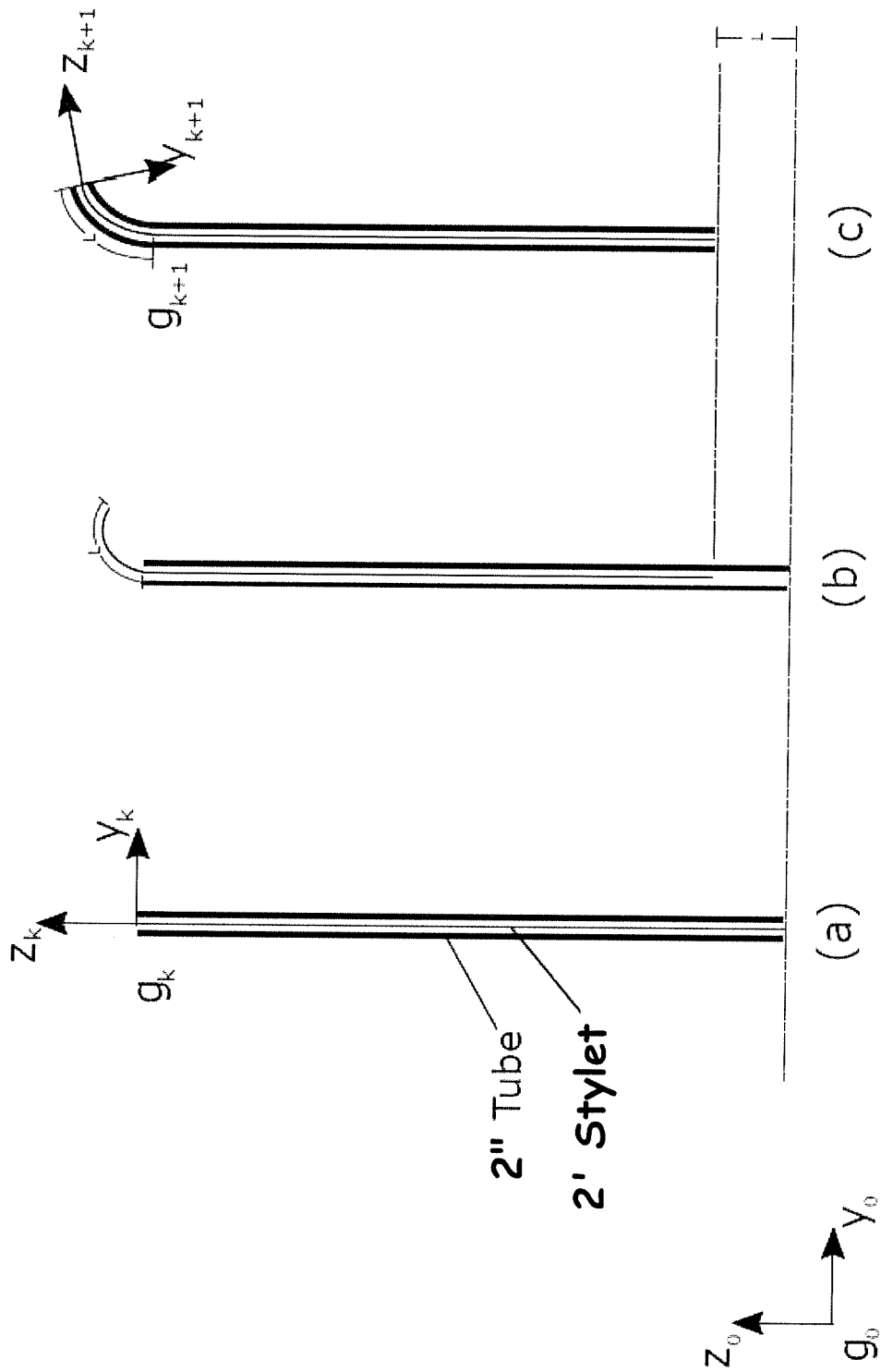
FIG. 9 shows shows the three distinct stages of needle insertion into the tissue for discussion of the modeling.

FIG. 9 again shows the three distinct stages of needle insertion into the tissue for ease of the following discussion. First, the stylet is extended out of the tube (see (b)), after which the tube follows the stylet (see (c)), as had been previously discussed. The z-axis of the body fixed frame is the direction of insertion. The arc length of each step is parameterized by 1, in millimeters. In order to find the position and orientation of needle with respect to the base frame, a model was developed for the relationship between the curvature, K, the step length, 1, and the rigid body motion FIG. 9(a), (c). The twist coordinates of the system are defined as follows:

$$\xi(l) = \begin{bmatrix} \omega \\ v \end{bmatrix} = \begin{bmatrix} \kappa(l) \\ 0 \\ 0 \\ 0 \\ 0 \\ 1 \end{bmatrix}$$

The twist describes the discrete-step needle motion and is a function of 1, which is the length of the stylet 2' that is inserted before the tube 2" follows. By inspection of the vector field defined by the twist, the needle 2 system has rotation around the body-fixed x-axis and linear translation along the z-axis. Using the matrix exponential of the twist describing the motion in each discrete step of the stylet and tube, the pose of the needle after a step can be calculated as the product of matrix exponential of the twist and the previous pose, $$g_{k+1} = e^{\xi kl} g_k$$

The discrete-step position/orientation change is only a function of the length of the needle that is inserted before the tube follows. The matrix $g_k \in SE(3)$ is the tube tip position/orientation before the needle is inserted and $g_{k+1} \in SE(3)$ is the tube tip position/orientation after the needle has been inserted and the tube has followed. This model can be used, based on experimentally determined curvature as a function of step length, K(1), to simulate needle 2 insertions for any number of steps and for any step-length along the way.

Simulation of Needle Insertion for Different Step Lengths

For Shape 1—Arc and the Shore 10M tissue simulant, the values of curvature for different values of step lengths are shown in Table 3.

TABLE 3

| Step length (mm) | Curvature (1/m) |
|---|---|
| 1 | 7.3481 |
| 2 | 10.1906 |
| 3 | 11.2625 |
| 4 | 14.1884 |
| 5 | 15.2207 |
| 6 | 20.7254 |

Curve fitting using MATLAB (The MathWorks, Inc., Natick, Mass., United States) showed that the relationship between curvature and step length can be approximated by a line with the following equation:

$$K = 0.00201 + 0.0057$$

Figure 10:
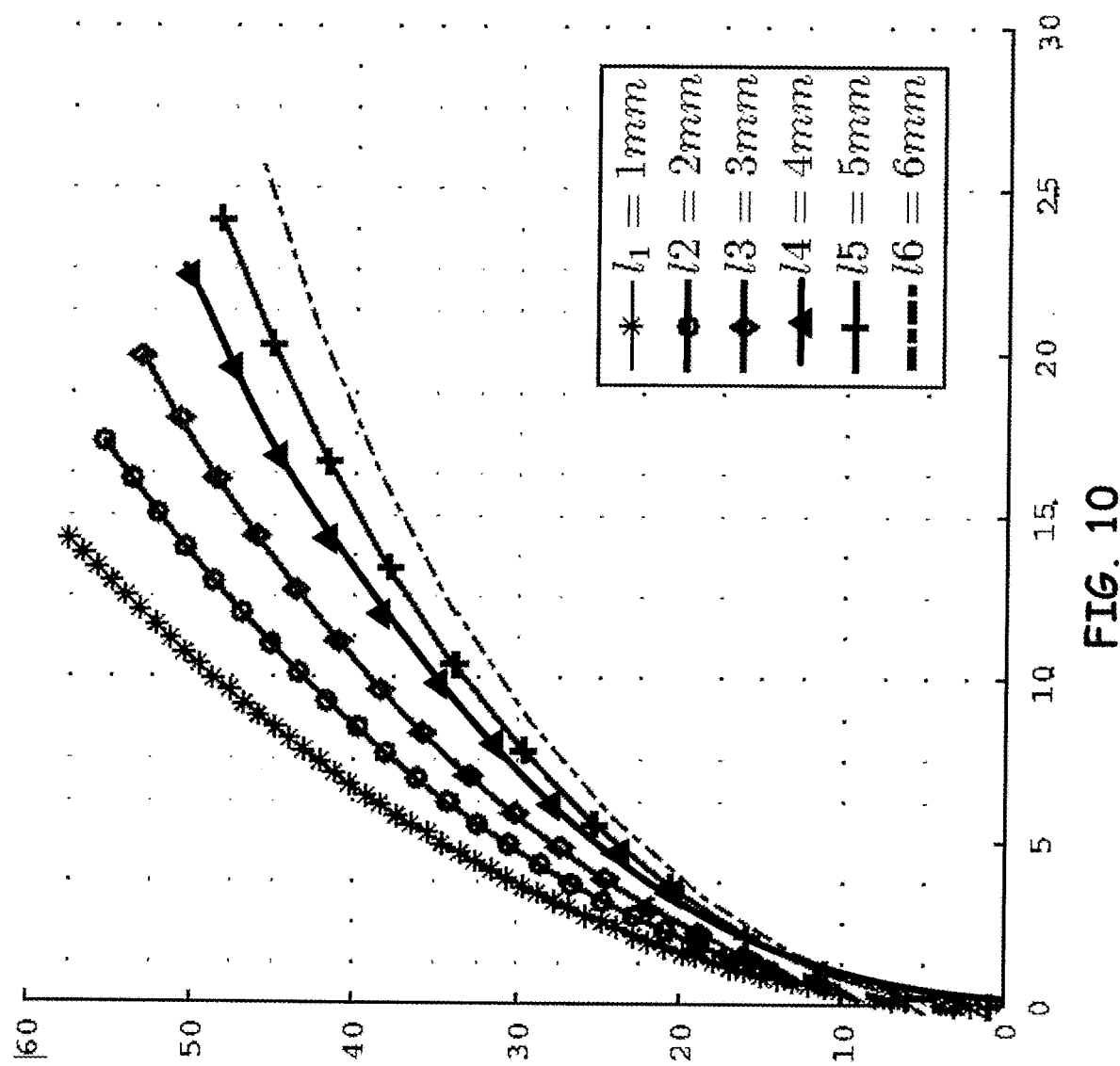
FIG. 10 shows the curvature change of a stylet being inserted into the tissue for different step lengths.

FIG. 10 thus depicts the curvature change of a needle (stylet 2') being inserted into the tissue for different step lengths. FIG. 10 shows that as the step length increases the amount of curvature of the needle will increase, thus decreased the radius of curvature. This linear relationship between the curvature and the step length of the stylet relative to the tube allows for precise control of the curvature across larger insertions. The consistency of FIGS. 5A-5F and FIG. 10 validates the model presented for the system.

Water Jet Embodiment

As another beneficial embodiment and as discussed above in the general description, the needle is re-configured as a water-jet (e.g., a pure/plain water jet (PWJ)) for the insertion applications as coupled to an actuator assembly, often but not necessarily, a linear actuator assembly similar to the stylet-needle embodiment briefly discussed above and as detailed herein. Without being bound by theory in practice of the invention, when no water jet is being used, the diameter of the needle is small enough that insertion similar to a standard needle is possible. Upon reaching a point where the needle needs to "steer" or make a turn, the angle of the nozzle is set to be directed to another direction by mechanical and/or magnetic means and a high-pressure, high-velocity stream of water is pulsed to cause a fracture in the tissue. Subsequent insertion of the needle causes the needle to follow the path of tissue fracture. Such a process is repeated as the needle needs to fracture and traverse the tissue. When utilized in, for example, a medical intervention, the fracture of tissue and following the fracture is to be provided a continuous process.

It is also to be noted, as discussed briefly above, water-jet cutting is beneficial because the water acts as a coolant and correspondingly, the temperature-related damages to the surrounding tissues is virtually non-existent, as seen with thermal ablation, grinding, or sawing. Second, water-jet cutting is precise, fast, and removes minimal material, where the water washes out the debris and leaves low-roughness surfaces. Using water-jet during surgery also decreases bleeding It is additionally to be appreciated that the nozzles at the tip of the configurations to provide the water-jet action, enables sub-millimeter cutting/fracturing that is also controllable using means to achieve high dexterity needle steering. To provide such sub-millimeter cutting/fracturing, the configurations of the diameters of the needles disclosed herein are often, but not necessarily about 0.75-1 mm, while the diameter of the nozzle is 1.5-2 mm, and wherein the outlet of the nozzle is about 120 microns up to about 200 microns in diameter. It is also to be understood without being bound be theory that while PWJ is often the desired mechanism/design, other water jet cutting mechanism/designs, such as, abrasive-water jet (AWJ) nozzles and coupled systems, can also be utilized without departing from the scope and spirit of the invention. In operation, the water-jet first controls the direction of tissue fracture and the needle then follows.

The water jet nozzle diameter at the outlet is reduced compared to the inlet and the accelerated water is forced through creating a focused jet stream. The last part of the outlet area is the steering configuration. It is to be noted that the nozzle at the tip is controlled to achieve a cutting angle of plus or minus 45 degrees in tip and/or tilt relative to the forward direction of the needle. Such a design provides for a minimally invasive method for procedures such as resections, excision, incision, or aspiration. This method would control needle steerability through first fracturing tissue in a prescribed direction and following with the needle. Control could be accomplished either through discrete steps or continuously. As part of controlling the nozzle tip, the nozzle can be configured of a rare earth magnet at the tip of the needle and an externally applied magnetic field of sufficient strength can thereafter redirect the nozzle tip. The purpose of having the nozzle fabricated from a magnet is to allow control of the nozzle angle by applying an external magnetic field. Nearly all biological tissues have a relative magnetic permeability close to 1.0. Hence, an externally applied magnetic field is a beneficial way to actuate the nozzle. Alternatively, but not bound by theory, cable actuation can be mechanical via the use of internal cabling, such as, but not limited to, a control wire or as another arrangement, a one to three tendon configuration wherein the tendons can be pulled to control the direction of the tip.

Water-Jet Experimental Set-up

A beneficial configuration utilized was a modification of the linear actuated system 100 of FIG. 1. Accordingly, the system though not detailed for this embodiment nonetheless uses a similar linear actuator to drive a needle 2 into tissue simulant with a speed that can be adjusted, using, for example a designed graphical user interface capable of not only communicating with and controlling the needle experiment but also read the force sensor and control a pump system through RS-232 over USB communications.

Such a user interface records data to a CSV file and is capable of feedback control. To allow high-fidelity control of volumetric flow rate and the ability to measure pressure at the pump, an example custom can be utilized but herein, an off-the shelf pump traditionally used for high-performance liquid chromatography (HPLC) was utilized (PR100PFT3D, Scientific Systems Inc., State College, Pa., USA). This system can provide pressures up to 4000 psi and flow rates up to 100 mL/min at the maximum pressure. Pure distilled water was used in this PWJ cutting system and a suction system attached to the end of needle avoids the water from splashing while inserting and cutting.

For the water jet nozzle, first a piece of, for example, 1=16" copper tubing is cut to about 4" of length. Then, a piece of Nitinol (or another suitable alloy, polymer or the like) is cut and sanded to remove for this material, the oxide layer so that the solder would adhere. Next, the Nitinol wire was soldered inside the 1=16" copper tubing. Finally, the copper tubing is attached to the ferruled reducer, and then to the water pump via standard HPLC PEEK tubing. While the force sensor records the insertion forces, a high resolution camera was used to take pictures during insertion or cutting experiments to measure the depth of cut as a function of fluid velocity. Image processing in Matlab measured the depth of cut from using a camera calibration to associate the pixels distance at the depth of cut inside the tissue simulant with real-world units.

Figure 11D:
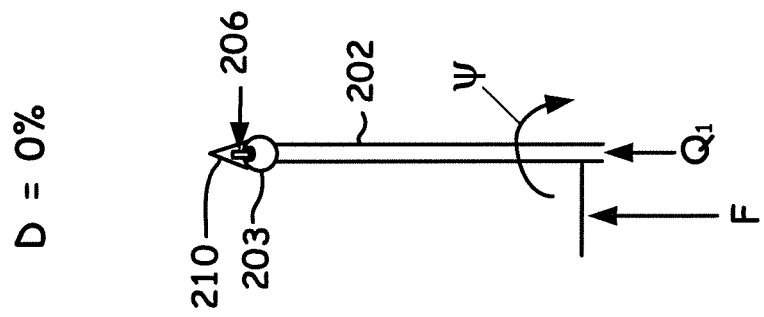
FIG. 11D also illustrates a needle and a sequence of actions that allow steering with a tip having a fixed angle for the nozzle.
Figure 11C:
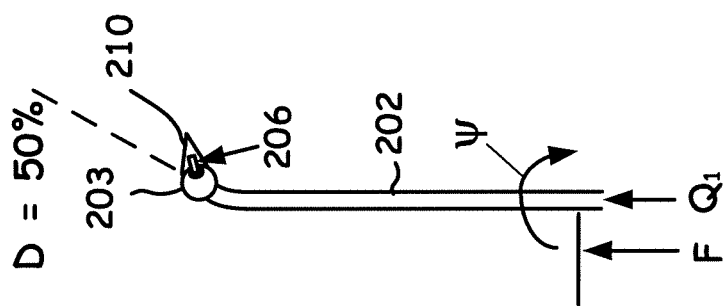
FIG. 11C also illustrates a needle and a sequence of actions that allow steering with a tip having a fixed angle for the nozzle.
Figure 11B:
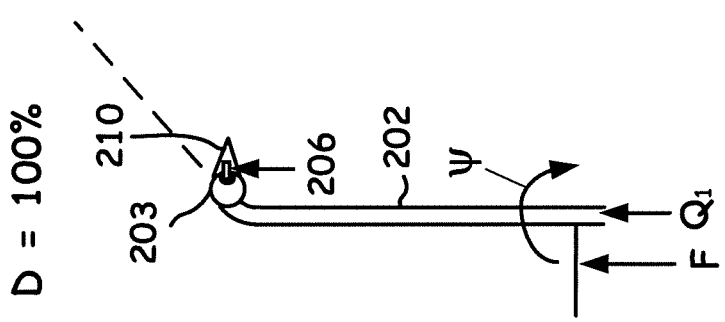
FIG. 11B also illustrates a needle and a sequence of actions that allow steering with a tip having a fixed angle for the nozzle.
Figure 11A:
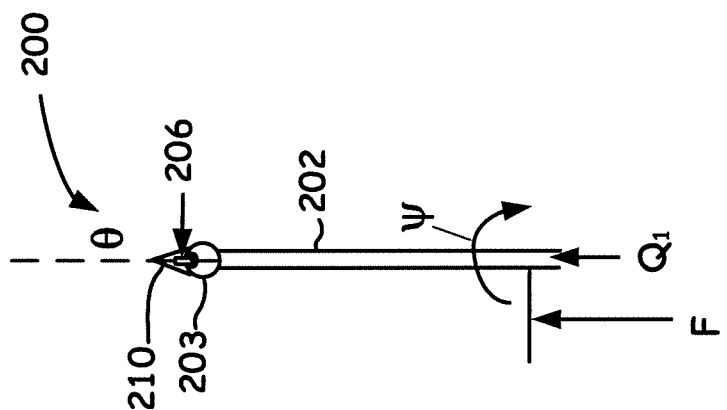
FIG. 11A illustrates a needle and a sequence of actions that allow steering with a tip having a fixed angle for the nozzle.

In a method of operation, FIG. 11A, FIG. 11B, FIG. 11C, and FIG. 11D illustrate a needle 200 and a sequence of actions that allow steering with a tip having a fixed angle for the nozzle, as discussed hereinafter. In the method, a cap is configured on the end of the needle 200 with a nozzle pointed at a fixed angle. FIG. 11A shows all the relevant parameters to include, a tip directional longitudinal axis (denoted as a dashed line) a needle tube 202 for fluid flow, a nozzle head 203, a directed water jet 206, a resultant fracture 210 in a tissue, a fixed nozzle head $\theta 0$, and control inputs to the system Q (volumetric fluid rate control) and F (the force or velocity applied at the base of the needle), the ratio of on vs off time of the water jet (duty cycle) D, the rotational angle $\Psi$ applied to the base of the needle.

In this method, the needle will either cut at the fixed angle theta $\theta$, if the waterjet is turned on with 100% or 50% duty cycling as shown in FIG. 11B and FIG. 11C for desired tissue fracturing while the needle is inserting, or travel straight when the waterjet is turned off (denoted as 0% duty cycled), as shown in FIG. 11D while the needle is inserted. The radius of curvature can be varied between the maximum radius of curvature (straight insertion) and the minimum radius of curvature (defined by theta), by rapidly controlling the ratio of on/off time of the water jet using D "duty cycling", as previously discussed for the stylet embodiment above.

FIG. 12A, FIG. 12B, FIG. 12C, and FIG. 12D illustrate an alternative method of operation wherein like reference numerals are utilized where warranted. Such a sequence of figures describes the actions that allows steering with the steerable needle that has a fully articulated nozzle at the tip. The particular methodology of actions are as follows: 1) the nozzle is rotated to control the direction the needle is pointing and the water jet is turned on or pulsed, 2) the waterjet thereafter cuts a small distance in front of the needle in the direction of the waterjet, 3) the needle is pushed from outside the tissue and the needle follows the direction where the waterjet cut the tissue, 4) the angle of the nozzle is continually updated to point in the direction the needle is desire to follow and the water jet is turned on or pulsed and wherein 5) this can be done either continuously or as a pulsed system (turning the water on and off between insertions). In this method, the control inputs to the system are: two angles representing the direction the needle is pointing: $\theta_1$ and $\theta_2$, the volumetric flow rate of the water Q, and the force or velocity applied at the base of the needle F.

Results

A. Force Measurement Results Using Insertions With and Without Water-Jet

Four different tests were done on each 77×29×30 mm, 15% and 20% SEBS tissues. First, the needle was inserted into the tissue with the speed of 8 mm/s using a linear actuator and without running the water-jet. The needle goes all the way through the tissue and for each displacement, force data was recorded using a customized Graphical User Interface (GUI). The data was recorded until the needle passes the tissue. The needle was then retracted and reinserted into the same channel using the same velocity of insertion and without water running and force data were recorded. Then, the pump is turned on with volumetric flow rate of 60 mL/min and this time, the needle is inserted with the same velocity of insertion along with the jet of water that cuts a small pass in front of the needle to let the needle pass the tissue. 10 experiments were done for each stage, with a total of 40 experiments for each tissue so 2×10×4=80 experiments were done and the average of 10 experiments and the standard deviation of data were calculated for each stage, so that the results were statistically meaningful.

Figures 13A, 13B:
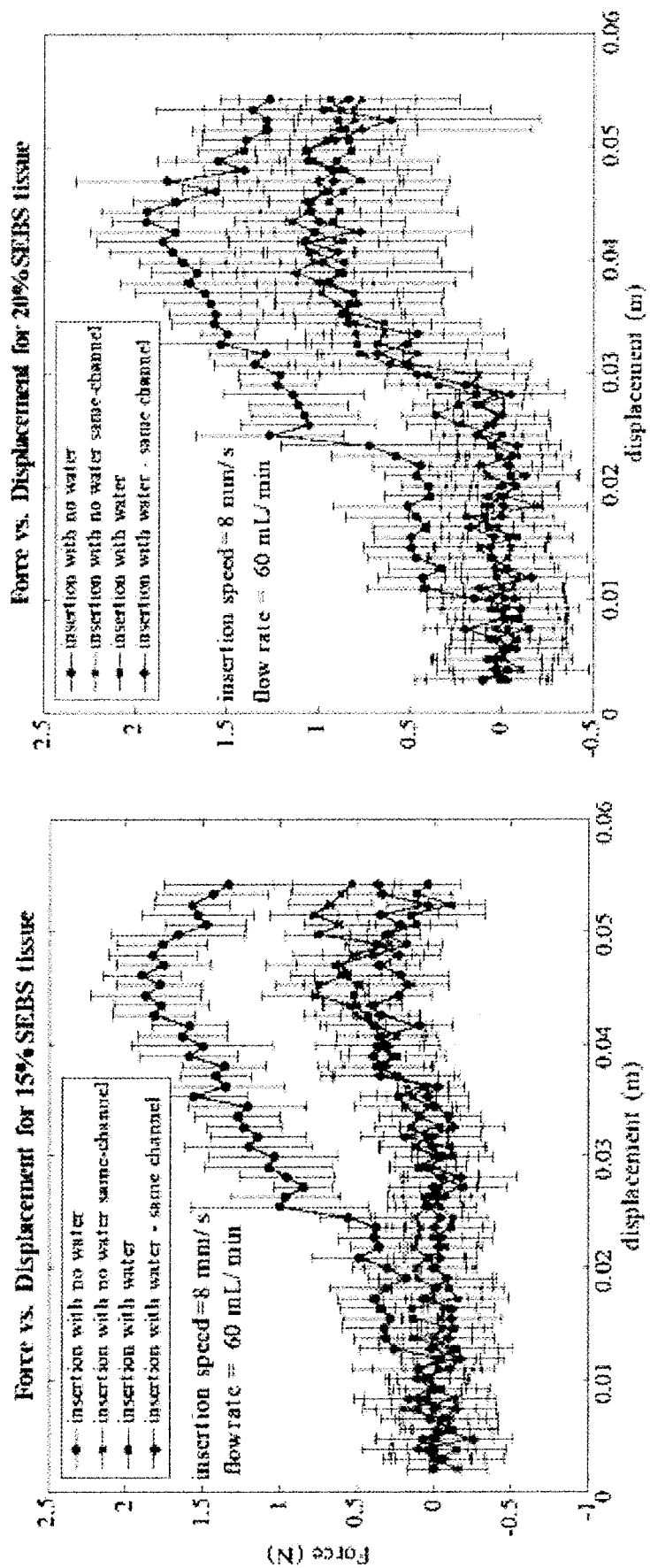
FIG. 13A shows Force vs. displacement measurements for ten trials in 15% SEBS tissue simulant. The water-jet eliminates the cutting force and only friction force exists.
FIG. 13B shows Force vs. displacement measurements for ten trials in 20% SEBS tissue simulant. The water-jet eliminates the cutting force and only friction force exists.
Figure 13C:
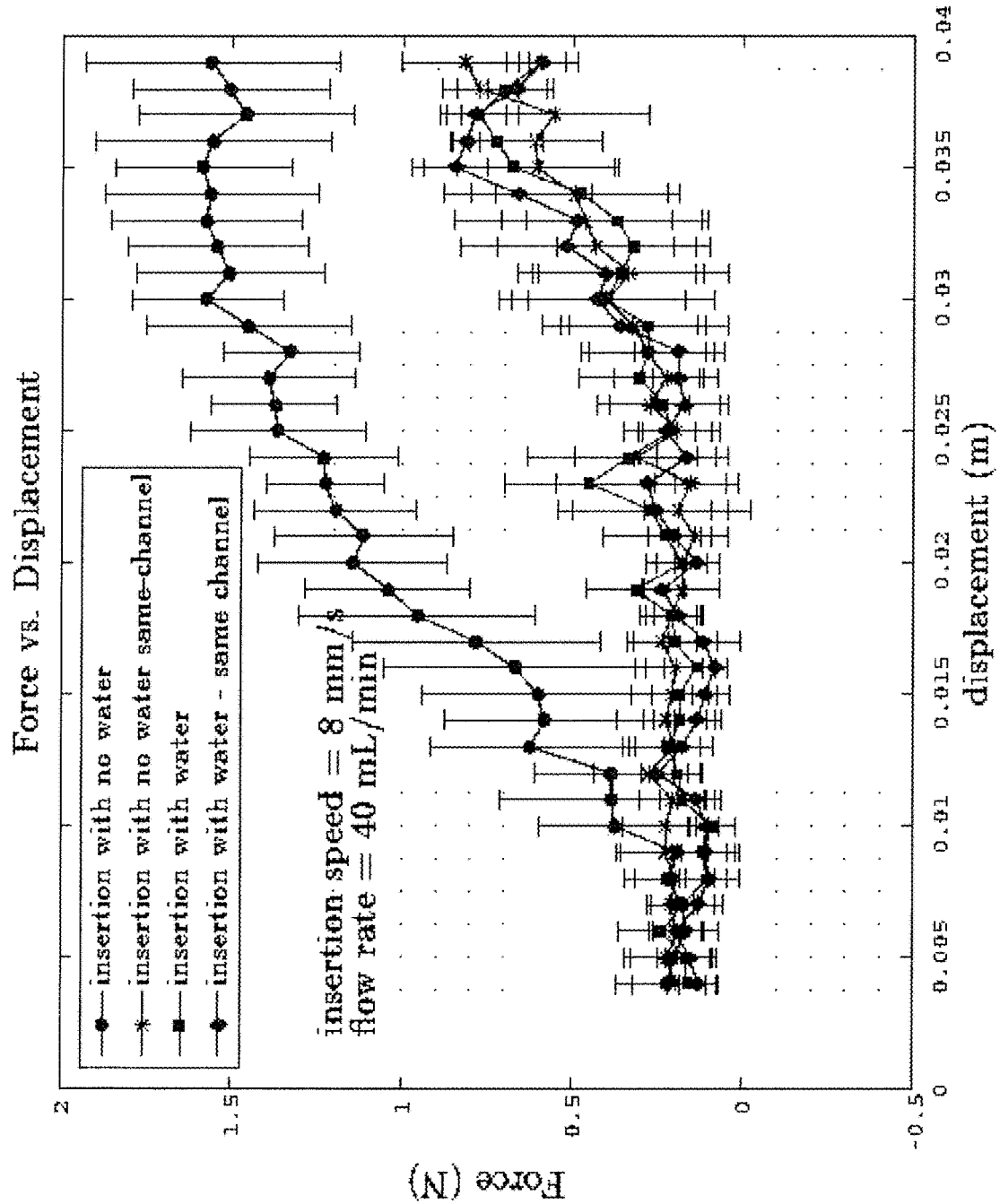
FIG. 13C also shows the force vs. displacement for insertions with no water, no water reinsertion through the same channel, with water-jet, and with water-jet reinsertion through the same channel but with a flow rate of 40 mL/min at a similar insertion speed of 8 mm/sec for comparison with the data shown in FIG. 13A and FIG. 13BS.

The average force from four different experiments on each tissue were plotted against the needle displacement. FIG. 13A, FIG. 13B and FIG. 13C show the force vs. displacement for insertions with no water, no water reinsertion through the same channel, with water-jet, and with water-jet reinsertion through the same channel. For additional comparison, FIG. 13A and FIG. 13B plots were obtained for 15%, 8 mm/sec insertion speed, flow rate=60 mL/min and 20% SEBS tissues while FIG. 13C data was using a flow rate of 40 mL/min at a similar insertion speed of 8 mm/sec for a comparison tissue. The bars on the figures represent one standard deviation above and one standard deviation below the data. The following results can be observed from these data:

- Comparing the forces in the case of insertions with no water and insertions with water-jet, it is apparent that water-jet gets rid of the cutting force and only the friction force exists. This will lead to increased accuracy of needle placement and comfort felt by patient.
- Needle passing through the tissue experiences different phases of cutting. In phase 1, tissue deflects and the force gradually rises. In phase 2, the tissue is cut and initial crack is formed. Needle geometry widens the crack and the needle passes through with friction acting between the needle and the tissue. In phase 3, the needle continues to pass through the tissue there is friction force between the outside of the needle and the tissue. For thicker tissues, there may be multiple deformation and cutting phases before the needle reaches its target location.

Maximum cutting force (F) is reached in phase 2, which is the total insertion force at puncture. This force can be divided into 2 different forces:

$$F = F_{elastic} + F_{friction}$$

In this equation, $F_{elastic}$ is the elastic force that fractures the tissue and forms a crack, and $F_{friction}$ is the friction force acting along the shaft of needle.

The 20% SEBS tissue has a higher frictional force. This is in agreement with Coulomb sliding friction where the friction is a function of a coefficient and the normal force (or really normal pressure across the surface area). In the case of the 20%, even though the needle is the same size and displacing the same amount of tissue, because it has a higher elastic modulus then the normal force/pressure will be higher for the same volume of tissue displaced by the needle.

Comparing the maximum cutting force of 15% and 20% tissues shows no significant difference. Even though the peak force is about the same, the cutting force is different. In the previous observation, the frictional force was greater for the 20% SEBS tissue. This means that in that peak force there is actually a more cutting force and a less friction force in the case of the 15%. It should be noted that often fracture toughness is not directly correlated with stiffness.

It does not appear that extra lubrication provided by the water-jet does reduce friction.

B. Depth of Cut of Water-Jet as a Function of Fluid Velocity

The needle is inserted about 2 cm into the 100×100×50 mm SEBS tissue. Using a high-resolution camera mounted above the tissue and using a light-box underneath the tissue, the before photo is taken. The pump was then turned on with a specific volumetric flow rate and after 30(s), the pump was turned off and another photo was taken showing the depth of cut of the water-jet in front of the needle. For better visibility, edible food colors were added to water. Volumetric flow rate was changed between 20 and 80 mL/min. For each flow rate, 5 experiments are conducted and the photos are processed using a customized Matlab program that measures the depth of cut in front of the needle from the pixels of the photo based on the calibrated measurement provided by the ruler on the light-box.

Figure 14B:
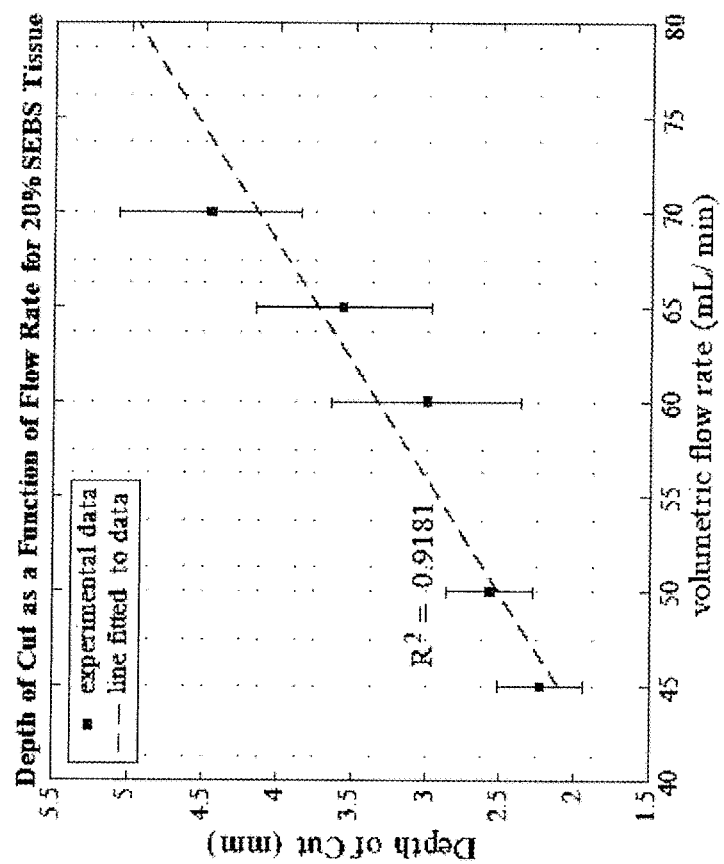
FIG. 14B shows depth of cut (DOC) for 20%. As can be seen there is a linear relationship between depth of cut and fluid velocity. 5 experiments were conducted for each flow rate and the average of them are reported. The bars on the graphs show one standard deviation above and below the mean.
Figure 14A:
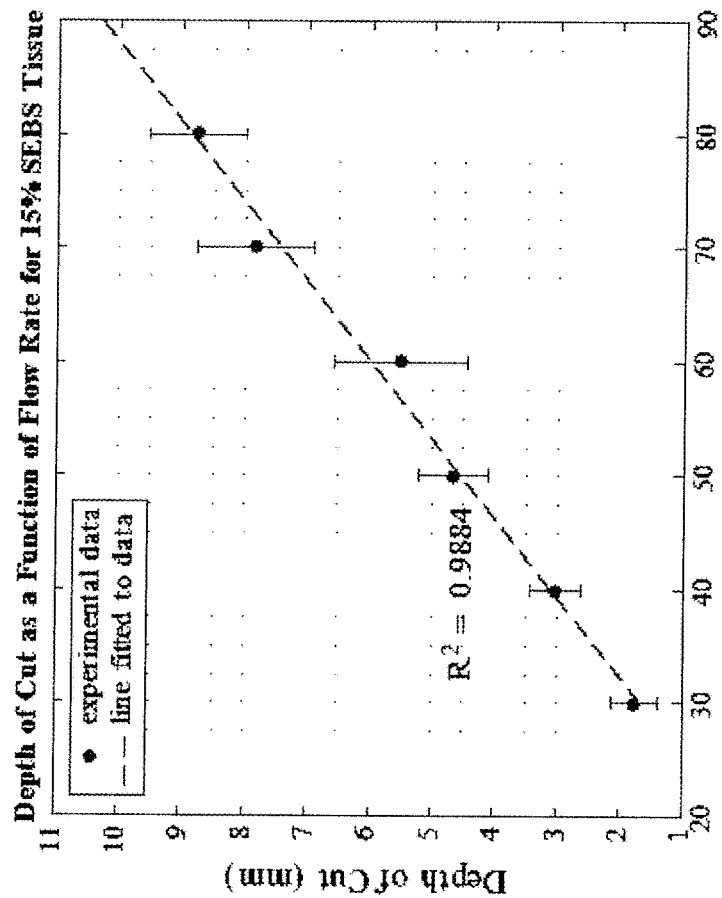
FIG. 14A shows depth of cut (DOC) for 15%. As indicated, there is a linear relationship between depth of cut and fluid velocity. The bars on the graphs show one standard deviation above and below the mean.

FIG. 14A and FIG. 14B depict the average measurements of depth of cut as a function of fluid velocity for 15% (up) and 20% (down) SEBS tissues. A line is fitted to experimental data and as can be seen the goodness of the fit, which is quantified by the coefficient of determination is 0:9884 for the 15% SEBS tissue, and 0:9181 for the 20% SEBS tissue. This gives a linear relationship between the depth of cut and the flow rate expressed by the DOC equation shown below, which can be used to predict the depth of cut (DOC) for higher flow rates when designing the configurations herein. The minimum flow rate (FR) that water-jet starts to cut the tissue depends on the stiffness of the tissue and is 30 mL/min in the case of 15% SEBS and 45 mL/min in the case of 20% SEBS tissue.

$$DOC = c_1(FR) + c_2$$

In this equation, $c1=0:1439$, and $c2=-2:653$ for 15% SEBS and $c1=0:08134$, and $c2=-1:553$ for 20% SEBS.

It should be emphasized that the above-described embodiments and the specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

I claim:

1. A fracture-directed method of steering a needle structure toward a desired target, comprising:
   a. inserting a needle structure within a tissue media, wherein the needle structure further comprises: a cannula fluid conduit coupled to a nozzle at a distal end, wherein the nozzle is configured to eject a desired fluid flow rate so as to provide a water jet;
   b. steering the nozzle away from the longitudinal axis of the cannula fluid conduit to control the needle structure direction such that the nozzle is not colinear with the cannula fluid conduit;
   c. pulsing or continuously providing the desired fluid flow rate to provide a fractured path within the tissue media in the direction of the water jet; then
   d. externally pushing the needle along the fractured path with a force;
   e. continually updating an angle of the nozzle so as to direct the needle to a determined path; and
   f. repeating steps b-e until the desired target is reached.

2. The method of claim 1, further comprising: providing the desired fluid flow rate at up to about 100 ml/min.

3. The method of claim 1, further comprising: controlling a nozzle tip cutting angle to plus or minus 45 degrees in tip and/or tilt relative to the forward direction of the needle structure.

4. The method of claim 1, further comprising: fixing the nozzle angle; thereafter alternating between i) fracturing the tissue media and following the fracture with the needle structure, and ii) preventing water jet cutting while pushing the needle.

5. The method of claim 1 wherein the nozzle at the tip has a fixed cutting angle and steerability is achieved through alternating between (a) fracturing tissue and following the fracture and (b) pushing the needle without water jet cutting.

6. The method of claim 1, further comprising: implementing up to a 100% duty cycle.

7. The method of claim 1, further comprising: rotating the nozzle angle or continually updating the nozzle angle includes using at least one of: a control wire, a tendon mechanism, and a magnetic field coupled to the nozzle.

8. The method of claim 1, wherein the diameter of the cannula fluid conduit is between 0.75 mm and 1 mm, the diameter of the nozzle is between 1.5 mm and 2 mm, and wherein an outlet of the nozzle is between 120 microns in diameter and 200 microns in diameter.

9. The method of claim 1, further comprising: feedback guidance of the needle structure in the tissue media using at least one of: ultrasound, fluorescence, tomography, computational sensor feedback, and magnetic resonance.

10. The method of claim 1, wherein the needle structure is configured from at least one material selected from Nitinol and a polymer.

* * * * *